United States Patent
Imawaka et al.

(10) Patent No.: US 7,579,375 B2
(45) Date of Patent: Aug. 25, 2009

(54) BRANCHED CARBOXYLIC ACID COMPOUND AND USE THEREOF

(75) Inventors: Haruo Imawaka, Mishima-gun (JP); Tomoyuki Hasegawa, Sakai-gun (JP); Shigeru Sakuyama, Sakai-gun (JP); Yasufumi Kawanaka, Sakai-gun (JP); Tsutomu Akiyama, Mishima-gun (JP); Masamitsu Hoshikawa, Mishima-gun (JP); Saiko Matsuda, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 68 days.

(21) Appl. No.: 10/564,720

(22) PCT Filed: Jul. 14, 2004

(86) PCT No.: PCT/JP2004/010366

§ 371 (c)(1),
(2), (4) Date: Jan. 17, 2006

(87) PCT Pub. No.: WO2005/005366

PCT Pub. Date: Jan. 20, 2005

(65) Prior Publication Data

US 2007/0167522 A1    Jul. 19, 2007

(30) Foreign Application Priority Data

Jul. 15, 2003    (JP) .............................. 2003-274988

(51) Int. Cl.
*A61K 31/20* (2006.01)
*C07C 59/00* (2006.01)
(52) U.S. Cl. ..................... 514/558; 554/213; 562/579
(58) Field of Classification Search .................. None
See application file for complete search history.

(56) References Cited

U.S. PATENT DOCUMENTS 6,201,021 B1 * 3/2001 Ohuchida et al. ........... 514/558

FOREIGN PATENT DOCUMENTS

| EP | 0 632 008 A1 | 1/1995 |
|---|---|---|
| EP | 1 415 668 A1 | 5/2004 |
| JP | 60-4182 A | 1/1985 |
| JP | 62-277375 A | 12/1987 |
| JP | 4-279576 A | 10/1992 |
| JP | 7-316092 A | 12/1995 |
| WO | WO 03/007992 A1 | 1/2003 |

OTHER PUBLICATIONS

Rettenmeier et al, Drug Metabolism and Disposition, Metabolic Fate of Valproic Acid in the Rhesus Monkey, 1986, 14(4), pp. 443-453.*
Manny et al, Tetrahedron, Reinvestigation of the Sulfuric Acid-Catalyzed Cyclisation of Brominated.2-Alkyllevulinic Acids to 3-Alkyl-5-methylene-2(5H)-furanones, 1997, 53(46), pp. 15813-15826.*
English et al, Journal of the American Chemical Society, The Synthesis of Some 1-Cyclopentenealdehydes, 1949, 71, pp. 3310-3313.*
Dobner et al, Chemistry and Physics of Lipids Synthesis of Deuterium-Labeled Methyl-branched Fatty Acids, 1991, 60(1), pp. 21-28, Abstract with STN printout.*
Yoneda et al, Chemistry Letters, Reaction Behavior of Carbon-Carbon and Carbon-Hydrogen Bonds in Super Acids, 1983, 1, pp. 19-20.*
Akopyan et al , Armayanskii Khimicheskii Zhurnal, 1976, 29(12), pp. 1039-1042, Abstract with STN printout.*
Dobner et al, Chemistry and Physics of Lipids Synthesis of Deuterium-Labeled Methyl-branched Fatty Acids, 1991, 60(1), pp. 21-28.*
Anthony J. Manny, et al., "Reinvestigation of the sulfuric acid-catalyzed cyclization of brominated 2-alkyllevulinic acids to 3-alkyl -5-methylene-2 (5H)-furanones, Tetrahdron", 1997, 15813 to 15826.
Howard T. Black, et al., "Synthesis of 3, 5-disubstituted butenolides. A short preparation of volatile streptomyces lactones, Synthetic Communications", 1995, 25 (4), 479-483.
Norihiko Yoneda, et al., "Reaction behavior of carbon-carbon and carbon-hydrogen bonds in super acids. Carboxylation of alkyl methyl ketones with carbon monoxide and water", Chemistry Letters, 1983, (1), 19-20.
Hermann Stetter, et al., "Addition of aldehydes to activated double bonds. XXV. Syntheses and reactions of branched tri-carbonyl compounds", Chemische Berichte, 1981, 114 (2), 564-580.
Tomoyuki Hasegawa, et al., "A practical synthesis of optically active (R) -2-propyloctanoic acid: therapeutic agent for Alzheimer's disease", Bulletin of the Chemistry Society of Japan, 2000. 73 (2), 423-428.
XP-002396106 (1977) Arzneim. Forsch., vol. 27 (Abstract).
B. Dobner et al. (XP-002396107 (1991) "Syntheses of deuterium-labeled methyl-branced fatty acids", Chemistry and Physics of Lipids (Abstract).
M. G. Zalinyan et al., XP-002396108 (1965) "Synthesis of unsaturated .delta.-lactones. II. Synthesis and reactions of 3-alkyl (benzyl)-6-methyl-3,4-dihydro-.alpha.-pyrones", Izvestiya Akademii Nauk Army Anskoi SSR (Abstract).

(Continued)

*Primary Examiner*—Paul A Zucker
(74) *Attorney, Agent, or Firm*—Sughrue Mion, PLLC

(57) ABSTRACT

The present invention relates to a compound represented by formula (I)

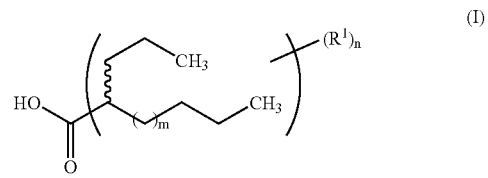

wherein $R^1$ represents optionally protected hydroxy or oxo, ∼∼∼indicates α-configuration, β-configuration or a mixture of these in an arbitrary proportion, n represents an integer of 1 to 3, and m represents 0 or an integer of 1 to 10; and wherein two or more $R^1$'s are not bound to the same carbon atom other than the terminal carbon atom, a salt thereof or a prodrug thereof. The compounds represented by formula (I) have an ability to improve astrocyte function, and they are useful as a preventive and/or therapeutic agent for a brain infarction, neuronal dysfunction by brain infarction, Parkinson's disease, Parkinson's syndrome, amyotrophic lateral sclerosis or Alzheimer's disease.

4 Claims, No Drawings

OTHER PUBLICATIONS

XP-002396109 (1969), Bull. Acad. Sci. USSR Div. Chem. Sci. (Abstract).
Herbert Koch et al., XP-002396110 (1965), "Dicarboxylic acids from undecylenic acid by carboxylation with acid catalysts", Brennstoff-Chemie (Abstract).
XP-002396111 (1970) J Org. Chem. USSR, No. 6 (Abstract).
XP-002396112 (1961) (Abstract).
XP-002396113 (1949) J. Am. Chem. Soc., vol. 71 (Abstract).
XP-002396123 (1961) Journal of Organic Chemistry, vol. 26 (Abstract).
John C Roberts et al., XP-008068105 (1950) "Synthesis of Potential Antibacterial Agents. Part 1. Some α- Alkylglutaric Acids and Their Derivatives", Journal of the Chemical Society, pp. 2842-2845.
J. W. et al., XP-002396114 (1981) "A dual role for GABA in quasi-morphine abstinence behavior induced by di-n-propylacetate involving both initiation and termination", Psychopharmacology (Abstract).
Kochen W. et al., XP-002396115 (1984) "Five doubly unsaturated metabolites of valproic acid in urine and plasma of patients on valproic acid therapy", Journal of Clinical Chemistry and Clinical Biochemistry (Abstract).
Kelem et al., XP-002396116 (1990) "Metabolic profiling of valproic acid in patients using negative-ion chemical ionization gas chromatography-mass spectrometry", Journal of Chromatography (Abstract).
G. I. et al., XP-002396117 (1961) "Free radical addition of carboxylic acids to vinyl and allyl acetates", Doklady Akademii Nauk SSSR (Abstract).
A. L. Voitsekhovskaya et al., XP-002396118 (1970) "Substituted lactones and their reactions. XV. Formation of . alpha.-alkyl-.delta.-methyl-.delta.-valerolactones from cyanoethylalkylacetoacetic esters", Zhurnal Organicheskoi Khimii (Abstract).
Anthony J. Manny et al., XP-002396119 (1997) "Reinvestigation of the sulfuric acid-catalyzed cyclization of brominated 2-alkyllevulinic acids to 3-alkyl-5-methylene-2(5H)-furanones", Tetrahedron (Abstract).
Salomon Piekarski et al., XP-008068112 (1961) "No. 218.—Dérivés α-substiués de acides aliphatiques normaux á longue chaine III.—Acides α-alkyllévuliques et α-alkyl β-acétylglurariques" (Abstract).
XP-002396120 (1977) Journal of Organic Chemistry, vol. 42, No. 15 (Abstract).
XP-002396121 (1960) J. Prakt. Chem., vol. 10 (Abstract).
XP-002396122 (1961) Aust. J. Chem., vol. 14 (Abstract).
Supplementary European Search Report dated Sep. 8, 2006.
Search Report from European Patent Office dated Nov. 23, 2007.

* cited by examiner

BRANCHED CARBOXYLIC ACID COMPOUND AND USE THEREOF

TECHNICAL FIELD

The present invention relates to a compound, which is useful for medicinal drug, represented by formula (I):

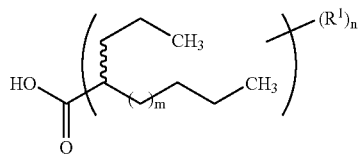

wherein all symbols have the same meanings as described below, use thereof, and a pharmaceutical composition comprising the same as an active ingredient.

BACKGROUND ART

It is reported that (2R)-2-propyloctanoic acid is useful for preventing and/or treating agent for neurodegenerative diseases such as brain infarction and Alzheimer's disease, since it has an ability to improve functions of astrocyte (see the specification of European Patent No. 0632008). Also, it is known that (2R)-2-propyloctanoic acid is useful for preventing and/or treating agent for Parkinson's disease or Parkinson's syndrome (see the specification of European Patent No. 1174131). Moreover, it is known that (2R)-2-propyloctanoic acid is useful for preventing and/or treating agent for cranial nerve diseases described hereinbefore, since it has an ability to decrease intracellular content of S100β to improve functions of astrocyte (see *The Journal of Cerebral Blood Flow & Metabolism*, 22, 723-734 (2002)). Furthermore, it is known that (2S)-2-propynylheptanoic acid derivatives functionate as a neurotrophic factor (see the specification of U.S. Pat. No. 5,672,746).

DISCLOSURE OF THE INVENTION

The compounds, which have so far been found, such as 2-propyloctanoic acid derivatives and (2S)-2-propynylheptanoic acid derivatives are not entirely satisfied. Because the compounds have pharmacological property for improvement such as intraoral acridity, or physico-chemical property for improvement such as side effect.

Thus, it is yearned for development of a useful cure for neurodegenerative diseases, which is improved in physico-chemical property, free of side effect, harmless, and which have an ability to improve functions of astrocyte, an ability to improve functions of brain, and/or an ability to decrease S100β expression.

As a result of the intensive study of the present inventors to solve the problem described above, it was found that the object was accomplished by novel compounds represented by the following formula (I), and thus the present invention has been completed.

That is, the present invention relates to
[1] a compound represented by formula (I):

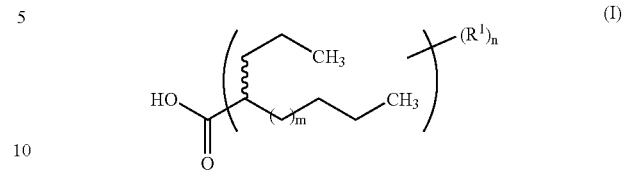

wherein
$R^1$ represents optionally protected hydroxy or oxo,
∼∼∼ indicates α-configuration, β-configuration or a mixture of these in an arbitary proportion,
n represents an integer of 1 to 3, and
m represents 0 or an integer of 1 to 10; and
wherein two or more $R^1$'s are not bound to the same carbon atom other than the terminal carbon atom,
a salt thereof or a prodrug thereof;
[2] the compound according to above [1], which is represented by formula (I-1):

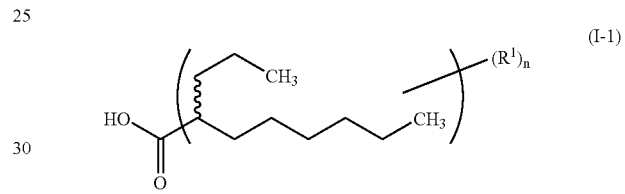

wherein all symbols have the same meanings as above [1];
[3] the compound according to above [1], which is represented by formula (I-1-1):

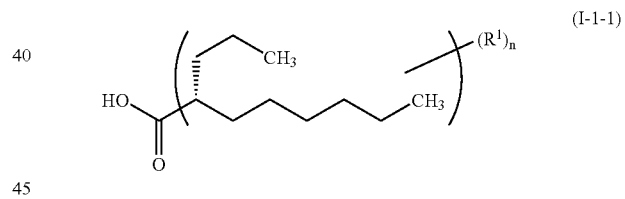

wherein
⋯⋯ indicates α-configuration, and
other symbols have the same meanings as in the above [1];
[4] the compound according to above [1], which is represented by formula (I-2):

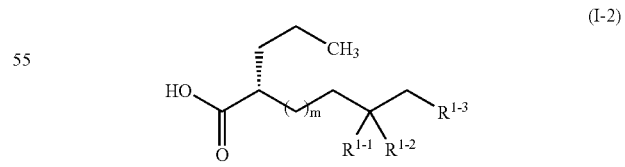

wherein
$R^{1-1}$ and $R^{1-2}$ are each independently a hydrogen atom or optionally protected hydroxy, or
$R^{1-1}$ is taken together with $R^{1-2}$ to represent oxo,
$R^{1-3}$ represents a hydrogen atom or optionally protected hydroxy, and other symbols have the same meanings as in the above [1] and [3], and wherein, when $R^{1-1}$ is taken together with $R^{1-2}$ to represent oxo, $R^{1-3}$ represents a hydrogen atom;

[5], the compound according to above [1], which is represented by formula (I-3):

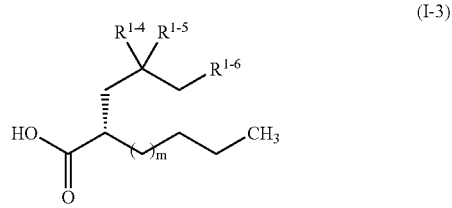

(I-3)

wherein
$R^{1-4}$ and $R^{1-5}$ are each independently a hydrogen atom or optionally protected hydroxy, or
$R^{1-4}$ is taken together with $R^{1-5}$ to represent oxo,
$R^{1-6}$ represents a hydrogen atom or optionally protected hydroxy, and
other symbols have the same meanings as in the above [1] and [3]; and
wherein, when $R^{1-4}$ is taken together with $R^{1-5}$ to represent oxo, $R^{1-6}$ represents a hydrogen atom;

[6] a compound represented by formula (I-2):

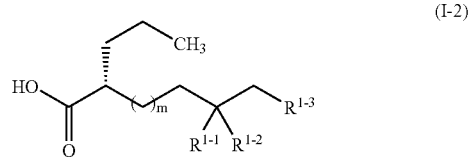

(I-2)

wherein
$R^{1-1}$ and $R^{1-2}$ are each independently a hydrogen atom or optionally protected hydroxy, or
$R^{1-1}$ is taken together with $R^{1-2}$ to represent oxo,
$R^{1-3}$ represents a hydrogen atom or optionally protected hydroxy,
m represents 0 or an integer of 1 to 10, and
⋯⋯""indicates α-configuration; and
wherein, $R^{1-1}$, $R^{1-2}$, and $R^{1-3}$ are not hydrogen atoms at the same time, and when $R^{1-1}$ is taken together with $R^{1-2}$ to represent oxo, $R^{1-3}$ represents a hydrogen atom,
a salt thereof or a prodrug thereof;

[7] the compound according to above [6], which is selected from the group consisting of (2R)-7-oxo-2-propyloctanoic acid, (2R,7R)-7-hydroxy-2-propyloctanoic acid, (2R,7S)-7-hydroxy-2-propyloctanoic acid and (2R)-8-hydroxy-2-propyloctanoic acid;

[8] the compound according to above [6], which is obtained by chemical synthesis;

[9] a pharmaceutical composition, which comprises the compound represented by formula (I) depicted in above [1], a salt thereof or a prodrug thereof;

[10] a pharmaceutical composition, which comprises the compound represented by formula (I-2) depicted in above [6], a salt thereof or a prodrug thereof;

[11] a preventive and/or therapeutic agent for a neurodegenerative disease, which comprises the compound represented by formula (I) depicted in above [1], a salt thereof or a prodrug thereof;

[12] a preventive and/or therapeutic agent for a neurodegenerative disease, which comprises the compound represented by formula (I-2) depicted in above [6], a salt thereof or a prodrug thereof;

[13] the preventive and/or therapeutic agent according to above [11] or [12], which is an improving agent of brain function, an improving agent of astrocyte function or an inhibiting agent of S100β expression;

[14] the preventive and/or therapeutic agent according to above [11] or [12], wherein the neurodegenerative disease is one or more of selected from the group consisting of Parkinson's disease, Parkinson's syndrome, Alzheimer's disease, Down's disease, amyotrophic lateral sclerosis, familial amyotrophic lateral sclerosis, progressive supranuclear palsy, huntington's disease, spinocerebellar degeneration, dentatorubral-pallidoluysian atrophy, olivopontocerebellar atrophy, corticobasal degeneration, dementia, Pick's disease, stroke, cerebrovascular disorder, multiple sclerosis, Guillain-Barre syndrome, acute disseminated encephalomyelitis, acute parencephalitis, transverse myelitis, brain tumor, cerebral meningitis, cerebral abscess, Creutzfeldt-Jakob disease and AIDS dementia complex;

[15] the preventive and/or therapeutic agent according to above [14], wherein the neurodegenerative disease is cerebrovascular disorder, Parkinson's disease, Parkinson's syndrome, amyotrophic lateral sclerosis or Alzheimer's disease;

[16] the preventive and/or therapeutic agent according to above [15], wherein the cerebrovascular disorder is brain infarction or neuronal dysfunction by brain infarction;

[17] a medicament, which comprises the compound represented by formula (I) depicted in above [1], a salt thereof or a prodrug thereof in combination with one or more of selected from the group consisting of an acetyicholinesterase inhibitor, a nicotinic receptor regulator, a β-secretase inhibitor, a gamma-secretase inhibitor, a β-amyloid protein aggregation inhibitor, a β-amyloid vaccine, a β-amyloid protease, a brain function activator, a cerebral blood flow and metabolism improver, a dopamine receptor agonist, monoamine oxidase inhibitor, an anticholinergic drug, a catechol-o-methyltransferase inhibitor, a curative medicine for amyotrophie lateral sclerosis, a neurotrophic factor, an apoptosis inhibitor, an antidepressant drug, an antianxiety drug, an anticonvulsant drug, an antihypertensive drug, a calcium receptor antagonist, a curative medicine for diabetes, a curative medicine for hyperlipidemia, an aldose reductase inhibitor, a nonsteroidal anti-inflammatory drug, a disease-modifying anti-rheumatic drug, an anticytokine drug, a steroid, an antithrombotic drug, a factor Xa inhibitor, a factor VIIa inhibitor, an antioxidant and a glycerite;

[18] the medicament depicted in above [17], wherein the antithrombotic drug is tissue plasminogen activator;

[19] a method for preventing and/or treating a neurodegenerative disease, which comprises administering to a mammal an effective amount of the compound represented by formula (I) depicted in above [1], a salt thereof or a prodrug thereof;

[20] use of the compound represented by formula (I) depicted in above [1], a salt thereof or a prodrug thereof for the manufacture of an agent for preventing and/or treating a neurodegenerative disease;

[21] a drug product which comprises the compound represented by formula (I) depicted in above [1], a salt thereof or a prodrug thereof;

[22] a drug product which comprises the compound represented by formula (I-2) depicted in above [6], a salt thereof or a prodrug thereof; and

[23] a process for preparation of the compound represented by formula (I) depicted in above [1], a salt thereof or a prodrug thereof.

In the specification, the improving agent of astrocyte function is a pharmaceutical composition which is useful for treating a disease(s) caused by the factor-induced neuronal injury, the factor which was released from astrocytes activated for some reason. This pharmaceutical composition has an action to normalize activated astrocytes, not only to inhibit astrocyte activation.

In the specification, "ring" in "optionally substituted ring" represented by $R^{10}$, $R^{11}$, $R^{12}$ or $R^{15}$ means, for example, carbocyclic ring and heterocyclic ring. Carbocyclic ring includes, for example, C3-15 mono-, bi- or tri-carbocyclic ring, spiro-fused bicarbocyclic ring and bridged bicarbocyclic ring. C3-15 mono-, bi- or tri-carbocyclic ring includes C3-15 mono-, bi- or tri-unsaturated carbocyclic ring and partially or fully saturated one. It includes, for example, cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indan, naphthalene, dihydronaphthalene, teterahydronaphthalene, perhydronaphthalene, heptalene, perhydroheptalene, biphenylene, as-indacene, s-indacene, acenaphthylene, acenaphthene, fluorene, phenalene, phenanthrene, anthracene, spiro[4.4]nonane, spiro[4.5]decane, spiro[5.5]undecane, bicyclo[2.2.1]heptane, bicyclo[2.2.1]hept-2-ene, bicyclo[3.1.1]heptane, bicyclo[3.1.1]hept-2-ene, bicyclo[3.2.1]octane, bicyclo[2.2.2]octane, bicyclo[2.2.2]oct-2-ene, adamantane, or noradamantane, etc. Among these, C3-15 mono-, bi- or tri-carbocyclic aromatic ring, includes, for example, benzene, azulene, naphthalene, phenanthrene, anthracene, etc.

Heterocyclic ring includes, for example, 3-15 membered mono-, bi- or tri-heterocyclic ring containing 1-5 hetero atom (s) selected from oxygen atom, nitrogen atom and/or sulfur atom, spiro-fused biheterocyclic ring and bridged biheterocyclic ring. 3-15 membered mono-, bi- or tri-heterocyclic ring includes 3-15 membered mono-, bi- or tri-unsaturated heterocyclic ring and partially or fully saturated one. It includes, for example, pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazan, benzothiadiazole, benzotriazole, carbazole, β-carboline, acridine, phenazine, dibenzofuran, xanthene, dibenzothiophene, phenothiazine, phenoxazine, phenoxathiin, thianthrene, phenanthridine, phenanthroline, perimidine, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole(oxazolidine), dihydroisoxazole, tetrahydroisoxazole(isoxazolidine), dihydrothiazole, tetrahydrothiazole(thiazolidine), dihydroisothiazole, tetrahydroisothiazole(isothiazolidine), dihydrofurazan, tetrahydrofurazan, dihydrooxadiazole, tetrahydrooxadiazole(oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, dioxaindan, benzodioxane, chroman, benzodithiolane, benzodithiane, etc. Spiro-fused biheterocyclic ring includes, for example, azaspiro[4.4]nonane, azaspiro[4.5]decane, etc. Bridged biheterocyclic ring includes, for example, azabicyclo[2.2.1]heptane, azabicyclo[3.1.1]heptane, azabicyclo[3.2.1]octane, azabicyclo[2.2.2]octane, etc. Among these, 3-15 mono-, bi- or tri-heterocyclic aromatic ring includes, for example, pyrrole, imidazole, triazole, tetrazole, pyrazole, pyridine, pyrazine, pyrimidine, pyridazine, furan, thiophene, oxazole, isoxazole, thiazole, isothiazole, furazan, oxadiazole, thiadiazole, indole, isoindole, benzofuran, isobenzofuran, benzothiophene, isobenzothiophene, indazole, quinoline, isoquinoline, purine, phthalazine, pteridine, naphthyridine, quinoxaline, quinazoline, cinnoline, benzoxazole, benzothiazole, benzimidazole, benzofurazan, benzothiadiazole, benzotriazole, carbazole, β-carboline, acridine, phenazine, dibenzofuran, dibenzothiophene, phenanthridine, phenanthroline, perimidine, etc.

"Substituent" in above "optionally substituted ring" means, for example, (a) optionally substituted alkyl, (b) optionally optionally substituted alkenyl, (c) optionally substituted alkynyl, (d) optionally substituted carbocyclic ring, (e) optionally substituted heterocyclic ring, (f) optionally substituted hydroxy, (g) optionally substituted thiol, (h) optionally substituted amino, (i) optionally substituted carbamoyl, (j) optionally substituted sulfamoyl, (k) carboxy, (l) alkoxycarbonyl (C1-6 alkoxycarbonyl such as methoxycarbonyl, ethoxycarbonyl, t-butoxycarbonyl), (m) sulfo, (n) sulfino, (o) phosphono, (p) nitro, (q) oxo, (r) thioxo, (s) cyano, (t) amidino, (u) imino, (v) —B(OH)$_2$, (w) halogen atom (e.g., fluorine atom, chlorine atom, bromine atom, iodine atom), (x) alkylsulfinyl (C1-6 alkylsulfinyl such as methylsulfinyl, ethylsulfinyl), (y) arylsulfinyl (C6-10 arylsulfinyl such as phenylsulfinyl), (z) alkylsulfonyl (C1-6 alkylsulfonyl such as methylsulfonyl, ethylsulfonyl), (aa) arylsulfonyl (C6-10 arylsulfonyl such as phenylsulfonyl), (bb) acyl (C1-10 alkanoyl such as formyl, acetyl, propanoyl, pivaloyl, C6-10 arylcarbonyl such as benzoyl). One to five substituent(s) among these optional substituents may be located at any position where substitution is possible.

"Alkyl" in "optionally substituted alkyl" means, for example, straight or branched C1-15 alkyl such as methyl, ethyl, propyl, isopropyl, butyl, isobutyl, sec-butyl, tert-butyl, pentyl, isopentyl, neopentyl, hexyl, heptyl, octyl, nonyl, decyl, undecyl, dodecyl, tridecyl, tetradecyl, pentadecyl, and the like. Here, the substituent of alkyl includes, hydroxy, amino, carboxy, nitro, mono- or di- C1-10 alkylamino (e.g., methylamino, ethylamino, propylamino, dimethylamino, diethylamino, and the like), C1-10 alkoxy (e.g., methoxy, ethoxy, propoxy, isopropoxy, t-butoxy, hexyloxy, octyloxy, decanyloxy, and the like), C1-10 alkylcarbonyloxy (e.g., acetoxy, ethylcarbonyloxy, and the like), carbocyclic ring (means the same as the above-mentioned carbocyclic ring in "ring" in "optionally substituted ring"), heterocyclic ring (means the same as the above-mentioned heterocyclic ring in "ring" in "optionally substituted ring"), halogen atom (fluorine atom, chlorine atom, bromine atom, iodine atom), C1-10 alkoxy substituted by 1 to 3 of halogen atom(s) (e.g., monofluoromethoxy, difluoromethoxy, trifluoromethoxy, and the like), —O-carbocyclic ring (means the same as the above-mentioned carbocyclic ring in "ring" in "optionally substituted ring"), and —O-heterocyclic ring (means the same as the above-mentioned heterocyclic ring in "ring" in "optionally substituted ring"). One to four substituent(s) among these optional substituents may be located at any position where substitution is possible.

"Alkenyl" as substituent in "optionally substituted alkenyl" means, for example, straight or branched C2-15 alkenyl such as ethenyl, propenyl, butenyl, butadienyl, pentenyl, pentadienyl, hexenyl, hexadienyl, heptenyl, heptadienyl, octenyl, octadienyl, nonenyl, nonadienyl, decenyl, decadienyl, undecenyl, dodecenyl, tridecenyl, tetradecenyl, pentadecenyl, and the like. Here, the substituent of alkenyl means the same as the above-mentioned substituents in "optionally substituted alkyl".

"Alkynyl" as substituent in "optionally substituted alkynyl" means, for example, straight or branched C2-15 alkynyl such as ethynyl, propynyl, butynyl, butadiynyl, pentynyl, pentadiynyl, hexynyl, hexadiynyl, heptynyl, heptadiynyl, octynyl, octadiynyl, nonynyl, nonadiynyl, decynyl, decadiynyl, undecynyl, dodecynyl, tridecynyl, tetradecynyl, pentadecynyl, and the like. Here, the substituent of alkynyl means the same as the above-mentioned substituents in "optionally substituted alkyl".

"Carbocyclic ring" as substituent in "optionally substituted carbocyclic ring" means the same as the above-mentioned carbocyclic ring in "ring" in "optionally substituted ring". Here, the substituent of carbocyclic ring includes, for example, straight or branched C1-10 alkyl (means the same as the above-mentioned alkyl in "optionally substituted alkyl"), straight or branched C2-10 alkenyl (means the same as the above-mentioned alkenyl in "optionally substituted alkenyl"), straight or branched C2-10 alkynyl (means the same as the above-mentioned alkynyl in "optionally substituted alkynyl"), hydroxy, C1-6 alkoxy (e.g., methoxy, ethoxy, propoxy, isopropoxy, butoxy, isobutyloxy, tert-butoxy, pentyloxy, hexyloxy, and the like), thiol, C1-6 alkylthio (e.g., methylthio, ethylthio, propylthio, isopropylthio, butylthio, isobutylthio, tert-butylthio, pentylthio, hexylthio, and the like), amino, mono- or di- C1-6 alkylamino (e.g., methylamino, ethylamino, propylamino, isopropylamino, butylamino, isobutylamino, tert-butylamino, pentylamino, hexylamino, dimethylamino, diethylamino, dipropylamino, N-methyl-N-ethylamino, and the like), halogen atom (means the same as the before-described), cyano, nitro, trifluoromethyl, trifluoromethoxy, and the like. One to five substituent(s) among these optional substituents may be located at any position where substitution is possible.

"Heterocyclic ring" as substituent in "optionally substituted heterocyclic ring" means the same as the above-mentioned heterocyclic ring in "ring" in "optionally substituted ring". Here, the substituent of heterocyclic ring means the same as the above-mentioned substituent(s) in "optionally substituted carbcyclic ring".

"Substituent" in "optionally substituted hydroxy", "optionally substituted thiol" and "optionally substituted amino" means, for example, (i) optionally substituted alkyl (means the same as described before), (ii) optionally substituted alkenyl (means the same as described before), (iii) optionally substituted alkynyl (means the same as described before), (iv) optionally substituted carbocyclic ring (means the same as described before), (v) optionally substituted heterocyclic ring (means the same as described before), (vi) acyl (C1-6 alkanoyl such as formyl, acetyl, propanoyl, pivaloyl, butanoyl, pentanoyl, hexanoyl or the isomer thereof or C6-10 carboarylcarbonyl such as benzoyl, and the like), (vii) optionally substituted carbamoyl (means the same as described later), (viii) alkylsulfonyl (C1-6 alkylsulfonyl such as methylsulfonyl, ethylsulfonyl, and the like), (ix) arylsulfonyl (C6-10 aryl sulfonyl such as phenylsulfonyl, and the like).

"Optionally substituted carbamoyl" as substituent means, for example, unsubstituted carbamoyl, N-mono-C1-6 alkylcarbamoyl (e.g., N-methylcarbamoyl, N-ethylcarbamoyl, N-propylcarbamoyl, N-isopropylcarbamoyl, N-butylcarbamoyl, N-isobutylcarbamoyl, N-(tert-butyl)carbamoyl, N-pentylcarbamoyl, N-hexylcarbamoyl, and the like), N-mono-C6-10 arylcarbamoyl such as N-phenylcarbamoyl, N,N-di-C1-6 alkylcarbamoyl (e.g., N,N-dimethylcarbamoyl, N,N-diethylcarbamoyl, N,N-dipropylcarbamoyl, N,N-dibutylcarbamoyl, N,N-dipentylcarbamoyl, N,N-dihexylcarbamoyl, N-methyl-N-ethylcarbamoyl, and the like), N-di-C6-10 arylcarbamoyl such as N,N-diphenylcarbamoyl, N-C6-10 aryl-N-C1-6 alkylcarbamoyl (e.g., N-phenyl-N-methylcarbamoyl, N-phenyl-N-ethylcarbamoyl, N-phenyl-N-propylcarbamoyl, N-phenyl-N-butylcarbamoyl, N-phenyl-N-pentylcarbamoyl, N-phenyl-N-hexylcarbamoyl, and the like).

"Optionally substituted sulfamoyl" as substituent means, for example, unsubstituted sulfamoyl, N-mono-C1-6 alkylsulfamoyl (e.g., N-methylsulfamoyl, N-ethylsulfamoyl, N-propylsulfamoyl, N-isopropylsulfamoyl, N-butylsulfamoyl, N-isobutylsulfamoyl, N-(tert-butyl)sulfamoyl, N-pentylsulfamoyl, N-hexylsulfamoyl, and the like), N-mono-C6-10 arylsulfamoyl such as N-phenylsulfamoyl, N,N-di-C1-6 alkylsulfamoyl (e.g., N,N-dimethylsulfamoyl, N,N-diethylsulfamoyl, N,N-dipropylsulfamoyl, N,N-dibutylsulfamoyl, N,N-dipentylsulfamoyl, N,N-dihexylsulfamoyl, N-methyl-N-ethylsulfamoyl, and the like), N-di-C6-10 arylsulfamoyl such as N,N-diphenylsulfamoyl, N-C6-10 aryl-N-C1-6 alkyl-sulfamoyl (e.g., N-phenyl-N-methylsulfamoyl, N-phenyl-N-ethylsulfamoyl, N-phenyl-N-propylsulfamoyl, N-phenyl-N-butylsulfamoyl, N-phenyl-N-pentylsulfamoyl, N-phenyl-N-hexylsulfamoyl, and the like).

In the specification, "optionally substituted alkyl" represented by $R^{10}$, $R^{11}$, $R^{12}$ or $R^{15}$ means the same as the above-mentioned "optionally substituted alkyl" in substituent in optionally substituted ring.

In the specification, "heterocyclic ring" formed by $R^{11}$ and $R^{12}$ in combination with nitrogen atom which bind them means, for example, 5-7 membered mono-cyclic heteroaryl ring containing 1-2 nitrogen atom(s), an oxygen atom and/or an sulfur atom, and partially or fully saturated one. It includes, for example, pyrrole, imidazole, pyrazole, pyrroline, pyrrolidine, imidazoline, imidazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, tetrahydrooxazole, tetrahydroisoxazole, tetrahydrothiazole, tetrahydroisothiazole, dihydrooxadiazole, tetrahydrooxadiazole, dihydrothiadiazole, tetrahydrothiadiazole, tetrahydrooxadiazine, tetrahydrothiadiazine, tetrahydrooxadiazepine, perhydrooxaazepine, perhydrooxadiazepine, tetrahydrothiadiazepine, perhydrothiazepine, perhydrothiadiazepine, morpholine, thiomorpholine.

In the specification, "protecting group" in "optionally protected hydroxy" represented by $R^1$, $R^{1-1}$, $R^{1-2}$, $R^{1-3}$, $R^{1-4}$, $R^{1-5}$, $R^{1-6}$, $R^{13}$ and $R^{14}$ means (i) optionally substituted alkyl (means the same as described before), (ii) optionally substituted alkenyl (means the same as described before), (iii) optionally substituted alkynyl (means the same as described before), (iv) optionally substituted carbocyclic ring (means the same as described before), (v) optionally substituted heterocyclic ring (means the same as described before), (vi) substituted silyl (e.g., trimethylsilyl, triethylsilyl, t-butyldimethylsilyl, t-butyldiphenylsilyl, and the like), (vii) optionally substituted acyl (C1-15 alkanoyl such as formyl, acetyl, propanoyl, pivaloyl, butanoyl, pentanoyl, hexanoyl, palmitoyl, dimethylaminomethylcarbonyl, alanyl, 2,2,2-trichloroethoxycarbonyl, or isomer thereof, and C6-10 carboarylcabonyl such as benzoyl, and the like), and the like. For example, hydroxy protected by protecting group which has leaving-group ability can be cited preferably. Hydroxy protected by protecting group which has leaving-group ability includes, for example, trityl, methoxymethyl (MOM), 1-ethoxyethyl (EE), methoxyethoxymethyl (MEM), benzyl (Bn), p-methoxybenzyl, 2-tetrahydropyranyl (THP), trimethylsilyl (TMS), triethylsilyl (TES), t-butyldimethylsilyl (TBDMS), t-butyldiphenylsilyl (TBDPS), acetyl (Ac), propanoyl, pivaloyl, palmitoyl, dimethylaminomethylcarbonyl, alanyl, 2,2,2-trichloroethoxycarbonyl (Troc), benzoyl, allyloxycarbonyl (Alloc), and the like.

In the specification, "C1-11 alkyl" represented by $R^{14}$ means, for example, straight or branched C1-11 alkyl such as methyl, ethyl, propyl, isopropyl, butyl, isobutyl, sec-butyl, tert-butyl, pentyl, isopentyl, neopentyl, hexyl, heptyl, octyl, nonyl, decyl, undecyl, and the like.

Among the compounds represented by formula (I), the compounds represented by formula (I-1):

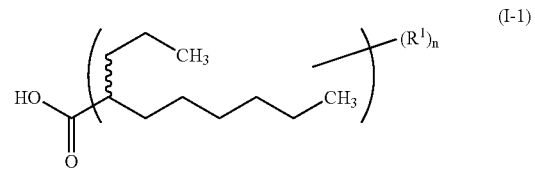

wherein all symbols have the same meanings as described before, the compounds represented by formula (I-2):

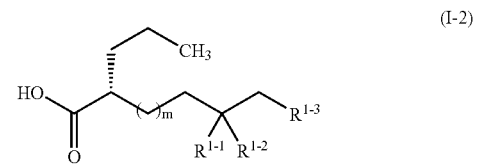

wherein all symbols have the same meanings as described before, and the compounds represented by formula (I-3):

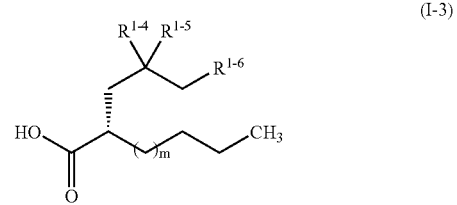

wherein all symbols have the same meanings as described before, salts thereof or prodrugs thereof can be cited preferably. More preferably, the compound represented by formula (I-2) can be cited.

Moreover, as the preferable compounds of the present invention represented by formula (I), for example, (2R)-7-oxo-2-propyloctanoic acid, (2R,7R)-7-hydroxy-2-propyloctanoic acid, (2R,7S)-7-hydroxy-2-propyloctanoic acid, (2R)-8-hydroxy-2-propyloctanoic acid, (2R)-2-propylsuberic acid, (2R)-6-hydroxy-2-propyloctanoic acid, (2R)-6-oxo-2-propyloctanoic acid, (2S)-2-(2-hydroxypropyl)octanoic acid, (2S)-2-(2-oxopropyl)octanoic acid and (2S)-2-(3-hydroxypropyl)octanoic acid, salts thereof or prodrugs thereof can be cited. More preferably, for example, (2R)-7-oxo-2-propyloctanoic acid, (2R,7R)-7-hydroxy-2-propyloctanoic acid, (2R,7S)-7-hydroxy-2-propyloctanoic acid and (2R)-8-hydroxy-2-propyloctanoic acid, salts thereof or prodrugs thereof can be cited. For example, (2R)-7-oxo-2-propyloctanoic acid and (2R)-8-hydroxy-2-propyloctanoic acid, salts thereof or prodrugs thereof can be most preferably cited.

In the present invention, unless otherwise specified, the symbol ⋯⋯means that the substituent attached thereto is behind the sheet (i.e., α-configuration), the symbol ▬means that the substituent attached thereto is in front of the sheet (i.e., β-configuration), the symbol ∼∼∼means α-configuration, β-configuration or a mixture of α-configuration and β-configuration, and the symbol ⎯⎯ means that there is a mixture of α-configuration and β-configuration as would be clear to the person skilled in the art.

A salt of the compound represented by formula (I) of the present invention includes all pharmaceutically acceptable salts. As the pharmaceutically acceptable salt, those which have no toxicity and are soluble in water are desirable. Suitable salts include, for example, salts of alkali metals (e.g., potassium, sodium, lithium, etc.), salts of alkaline earth metals (e.g., calcium, magnesium, etc.), ammonium salts (e.g., tetramethyl ammonium salt, tetrabutylammonium salt, etc.), salts of organic amines (e.g., triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine, etc.), acid addition salts [salts of inorganic acids (e.g., hydrochloride, hydrobromide, hydroiodide, sulfate, phosphate, nitrate, etc.), salts of organic acids (e.g., acetate, trifluoroacetate, lactate, tartrate, oxalate, fumarate, maleate, citrate, benzoate, methanesulfonate, ethanesulfonate, benzenesulfonate, toluenesulfonate, isethionate, glucuronate, gluconate, etc.), etc.]. A salt of the compound of the present invention include solvates, and solvates of alkaline (earth) metal salts, ammonium salts, organic amine salts, or acid addition salts of the compounds of the present invention. The solvates are preferably non-toxic and soluble in water. Suitable solvates include, for example, a solvate water or an alcoholic solvent (e.g., ethanol, etc.). The compound of the present invention may be converted into the pharmaceutically acceptable salt by the known method. Moreover, a quaternary ammonium salt are included in the salts of the present invention.

Also, the prodrugs of the compounds represented by formula (I) are those which can be converted into the compounds of the formula (I) of the present invention by the in vivo action of enzymes or gastric acid. Examples of the prodrugs of compounds represented by formula (I) are (1) those wherein the hydroxy group is acylated, alkylated, phosphorylated, or borated (for example, compounds wherein the hydroxy group is acetylated, palmitoylated, propanoylated, pivaloylated, succinylated, fumarylated, alanylated, dimethylaminocabonylated, etc.), when compounds represented by formula (I) contain a hydroxy group; and (2) those wherein the carboxyl group is esterified, or amidated (for example, compounds wherein the carboxyl group is converted into an ester such as ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, and cyclohexyloxycarbonylethyl ester, or compounds which are methylamidated). These compounds can be prepared by the conventional method. The prodrug of the compound represented by formula (I) may include hydrates and non-hydrates.

For example, the prodrug of the compound represented by formula (I) includes, the compounds represented by formula (II):

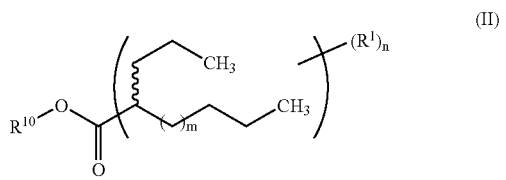

wherein $R^{10}$ represents optionally substituted alkyl or optionally substituted ring, and other symbols have the same meanings as described before, the compounds represented by formula (III):

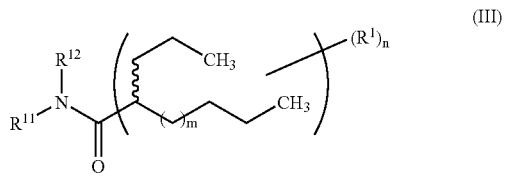

wherein $R^{11}$ and $R^{12}$ are each independently, hydrogen atom, optionally substituted alkyl or optionally substituted ring, or $R^{11}$ and $R^{12}$ are taken together with nitrogen atom which bound them to represent heterocyclic ring, and other symbols have the same meanings as described before, the compounds represented by formula (IV):

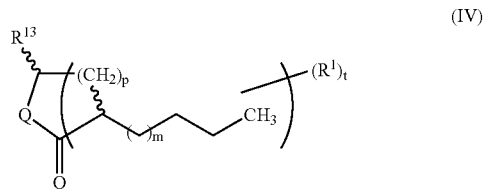

wherein t represents 0 or an integer of 1 to 2, p represents 1 or 2, $R^{13}$ represents (1) hydrogen atom, (2) hydroxy, or (3) optionally protected hydroxy or methyl substituted by oxo, Q represents —O— or —$NR^{15}$— ($R^{15}$ represents optionally substituted alkyl or optionally substituted ring), and other symbols have the same meanings as described before, and wherein, in formula (IV), the total number of carbon atom is 8 to 18 and the total number of optionally protected hydroxy or oxo is 0 or 1 to 2, and the compounds represented by formula (V):

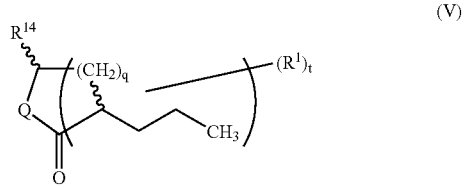

wherein q represents an integer of 1 to 12, $R^{14}$ represents (1) hydrogen atom, (2) hydroxy or (3) C1-11 alkyl which is optionally substituted by optionally protected hydroxy or oxo, and other symbols have the same meanings as described before, and wherein, in formula (V), the total number of carbon atom is 8 to 18 and the total number of optionally protected hydroxy or oxo is 0 or 1 to 2.

The compound represented by formula (I) of the present invention excels in solubility and absorbability. Also, the compound of the present invention inhibit drug-metabolizing enzyme weakly. These properties are most important physical, chemical, or pharmaceutical properties which are requested at the developmental stage of medicinal drugs, so the compound of the present invention has the properties enough to be good medicinal drugs (see "The Merck Manual of Diagnosis and Therapy" (17th Ed), Merck & Co.).

Process for the Preparation of the Compound of the Present Invention

The compound of the present invention represented by formula (I) can be prepared by the known method, for example, the method written in the specification of EP0632008, WO99/58513, WO00/48982, WO03/051852 or WO03/097851, or the method written in Comprehensive Organic Transformations (A Guide to Functional Group Preparations, 2nd edition, Richard C. Larock, John Wiley & Sons Inc, 1999), or the method described below, and/or the method based on them. If desired, these methods may be improved or combined. In addition, the starting material in each preparation method described below may be used in the form of a salt. Such salt used is the salt of compounds represented by formula (I) as defined above.

The compounds represented by formula (I) can be prepared by subjecting a compound represented by formula (2):

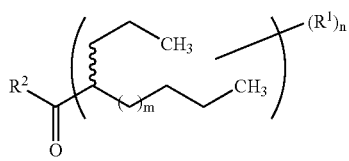

wherein $R^2$ represents C1-8 alkoxy (e.g., methoxy, ethoxy, propoxy, hexyloxy, octyloxy, t-butyloxy and the like), a group represented by formula (2-1):

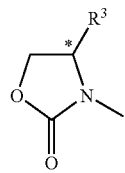

wherein $R^3$ represents isopropyl or benzyl, * represents asymmetric carbon atom, or a group represented by formula (2-2):

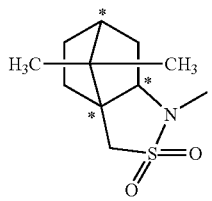

and other symbols have the same meanings as described before,
to a hydrolysis reaction, followed by a deprotection reaction of a hydroxy group, if necessary.

This hydrolysis reaction is known. For example, when $R^2$ represents C1-8 alkoxy, alkaline hydrolysis or hydrolysis under acidic conditions is used. Alkaline hydrolysis is, for example, carried out in an organic solvent (e.g., methanol, tetrahydrofuran, dioxane, etc.) using a hydroxide of an alkali metal (e.g., sodium hydroxide, potassium hydroxide, lithium hydroxide, etc.), a hydroxide of an alkali earth metal (barium hydroxide or calcium hydroxide, etc.), a carbonate (e.g., sodium carbonate or potassium carbonate, etc.), an aqueous solution thereof, or a mixture thereof at a temperature of 0 to 40° C. Hydrolysis under acidic conditions is carried out, for example, in an organic solvent (e.g., methanol, tetrahydrofuran, dioxane, etc.) using an organic acid (e.g., acetic acid, trifluoroacetic acid, methanesulfonic acid, p-tosylic acid, etc.), an inorganic acid (e.g., hydrochloric acid, sulfuric acid, etc.), a mixture thereof (e.g., hydrogen bromide/acetic acid, etc.), an aqueous solution thereof, or a mixture thereof at a temperature of 0 to 100° C. When $R^2$ represents a group represented by formula (II-1), for example, in an organic solvent (e.g., tetrahydrofuran, ethylene glycol dimethyl ether, etc.), in the presence or absence of peracid (e.g., hydrogen peroxide, t-butylhydroperoxide, or an aqueous solution thereof, etc.), using tetraalkylammonium hydroxide (e.g., benzyltrimethylammonium hydroxide, tetraethylammonium hydroxide, tetraisopropyl ammonium hydroxide, tetrabutylammonium hydroxide, tetraoctylammonium hydroxide or an aqueous solution thereof, etc.) at a temperature of −20 to 40° C. For example, when $R^2$ represents a group represented by formula (II), it is carried out by a method using (i) hydroxide of an alkali metal, or (ii) tetraalkylammonium hydroxide.

(i) a method using hydroxide of an alkali metal is known (see Tetrahedron, 43 1969 (1987) and Helv. Chim. Acta., 72, 1337 (1989)). For example, it is carried out in a water-miscible solvent (e.g., tetrahydrofuran, dioxane or mixed solvent thereof with water, etc.), in the presence or absence of peracid (e.g., hydrogen peroxide, t-butylhydroperoxide, or an aqueous solution thereof, etc.), using hydroxide of an alkali metal (e.g., lithium hydroxide, sodium hydroxide, potassium hydroxide, or an aqueous solution, etc.) at a temperature of 0 to 40° C.

(ii) a method using tetraalkylammonium hydroxide is known (see the specification of WO99/158513). For example, it is carried out in a water-miscible solvent (e.g., tetrahydrofuran, dimethoxyethane, t-butanol, dioxane or mixed solvent thereof with water, etc.), in the presence or absence of peracid (e.g., hydrogen peroxide, t-butylhydroperoxide, or an aqueous solution thereof, etc.), using tetraalkylammonium hydroxide (e.g., tetrabutylammonium hydroxide, tetraoctylammonium hydroxide, tetradecylammonium hydroxide, or an aqueous solution thereof, etc.) at a temperature of −20 to 40° C. Also, when the compound has double bond or triple bond, in order to prevent an oxidation of double bond or triple bond by peracid, the reaction is carried out under the presence of an excess of compound which have double bond (e.g., 2-methyl-2-butene).

Deprotection reaction of a protective group for hydroxy is known and its examples are as follows.

(1) a hydrolyzing reaction with an alkali;
(2) a deprotection reaction under an acidic condition;
(3) a deprotection reaction by hydrogenolysis;
(4) a deprotection reaction of silyl;
(5) a deprotection reaction using metal; and
(6) a deprotection reaction using an organic metal.

Those methods will be specifically illustrated as follows.
(1) A hydrolyzing reaction with an alkali is carried out, for example, by the same method as an alkaline hydrolysis.
(2) A deprotection reaction under an acidic condition is carried out, for example, by the same method as a hydrolysis under acidic conditions.
(3) A deprotection reaction by hydrogenolysis is carried out, for example, at the temperature of 0 to 200° C. in a hydrogen atmosphere of ordinary pressure or high pressure or in the presence of ammonium formate in the presence of a catalyst (such as palladium-carbon, palladium black, palladium hydroxide, platinum oxide and Raney nickel) in a solvent [such as an ether type (such as tetrahydrofuran, 1,4-dioxane, dimethoxyethane and diethyl ether), an alcohol type (such as methanol and ethanol), a benzene type (such as benzene and toluene), a ketone type (such as acetone and methyl ethyl ketone), a nitrile type (such as acetonitrile), an amide type (such as N,N-dimethylformamide), water, ethyl acetate, acetic acid or a mixed solvent comprising two or more thereof].

(4) A deprotection reaction of silyl is carried out, for example, at the temperature of 0 to 40° C. using tetrabutylammonium fluoride in a water-miscible organic solvent (such as tetrahydrofuran and acetonitrile, etc.).

(5) A deprotection reaction using metal is carried out, for example, at the temperature of 0 to 40° C. with or without ultrasonic wave in the presence of powdery zinc in an acidic solvent (such as acetic acid, a buffer of pH 4.2 to 7.2 or a mixed solution of a solution thereof with an organic solvent such as tetrahydrofuran).

(6). A deprotection reaction using a metal complex is carried out, for example, at the temperature of 0 to 40° C. using a metal complex [such as tetrakistriphenylphosphine palladium (0), bis(triphenylphosphine)palladium (II) dichloride, palladium (II) acetate and tris(triphenylphosphine) rhodium (I) chloride] in the presence or absence of a phosphine agent (such as triphenyl phosphine) in the presence of a trap reagent (such as tributyltin hydride, triethylsilane, dimedone, morpholine, diethylamine and pyrrolidine), an organic acid (such as acetic acid, formic acid and 2-ethylhexanoic acid) and/or an organic acid salt (such as sodium 2-ethylhexanoate and potassium 2-ethylhexanoate) in an organic solvent (such as dichloromethane, N,N-dimethylformamide, tetrahydrofuran, ethyl acetate, acetonitrile, 1,4-dioxane and ethanol), water or a mixed solvent thereof.

Besides the above-mentioned method, for example, a deprotection reaction may be carried out by a method mentioned in T. W. Greene, *Protective Groups in Organic Synthesis*, John Wiley & Sons Inc, 1999. As persons skilled in the art can easily understand that the aimed compound of the present invention is able to be easily produced by using appropriate ones among those deprotection reactions.

Among the compounds represented by formula (I), a compound in which $R^1$ represents oxo, namely, a compound represented by formula (I-A):

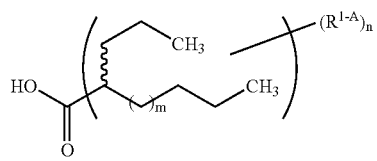

wherein $R^{1-A}$ represents oxo, and other symbols have the same meanings as described above, can be prepared by subjecting a compound, prepared by before-described method, in which $R^1$ represents hydroxy, represented by formula (I-B):

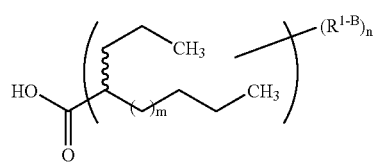

wherein $R^{1-B}$ represents hydroxy, and other symbols have the same meanings as described above, to a oxidation reaction.

This oxidation reaction is known. For example, it is carried out by a method using (1) Swern oxidation, (2) Dess-Martin Reagent or (3) TEMPO reagent. Those methods will be specifically illustrated as follows.

(1) The method using Swern oxidation is carried out, for example, reacting oxalyl chloride with dimethyl sulfoxide in an organic solvent (e.g., chloroform, dichloromethane) at −78° C., and then reacting the resulting solution with the alcohol compound, and further with a tertiary amine (e.g., triethylamine, N,N-diisopropylethylamine, N-methylmorpholine, N-ethylpiperidine, diazabicyclo[5.4.0]undec-7-ene) at −78 to 20° C.

(2) The method using a Dess-Martin reagent is carried out, for example, in an organic solvent (e.g., chloroform, dichloromethane, 1,2-dichloroethane, tetrahydrofuran, acetonitrile, t-butyl alcohol) in the presence of a Dess-Martin reagent (1,1,1-triacetoxy-1,1-dihydro-1,2-benzoiodoxol-3-(1H)-one), in the presence or absence of a base (e.g., pyridine) at 0 to 40° C.

(3) The method using a TEMPO reagent is carried out, for example, in an organic solvent (e.g., chloroform, dichloromethane, tetrahydrofuran, toluene, acetonitrile, ethyl acetate, water, etc.) or in a mixed solvent thereof, in the presence of a TEMPO reagent (2,2,6,6-tetramethyl-1-piperidinyloxy, free radical) and a re-oxidizing agent (aqueous hydrogen peroxide, sodium hypochlorite, 3-chloroperbenzoic acid, iodobenzene diacetate, potassium peroxymonosulfate (Oxone, trade name)), in the presence or absence of a quaternary ammonium salt (e.g., tetrabutylammonium chloride, tetrabutylammonium bromide), in the presence or absence of an inorganic salt (e.g., sodium bromide, potassium bromide), in the presence or absence of an inorganic base (e.g., sodium hydrogencarbonate, sodium acetate), at 20 to 60° C.

The oxidation is not limited to the above, and may be any other capable of readily and selectively oxidizing. For example, herein employable is any of Jones' oxidation, oxidation with PCC (pyridinium chlorochromate), oxidation with sulfur trioxide-pyridine complex, or those described in *Comprehensive Organic Transformations* (Richard C. Larock, VCH Publishers, Inc., (1989)).

Among the compounds represented by formula (I), a compound in which two of $R^1$'s are bound to same terminal carbon atom, and they represent oxo and hydroxy (namely, a compound in which the terminal carbon atom is substituted by carboxy group), namely, represented by formula (I-C):

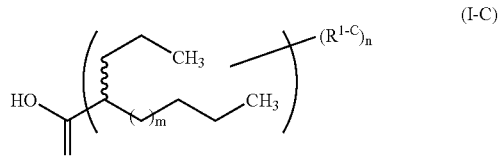

wherein $R^{1-C}$ represents carboxy substituted in terminal carbon atom, and other symbols have the same meanings as described above, can be prepared by subjecting a compound represented by formula (I-B) to a oxidation reaction.

The above oxidation reaction is known. For example, (1) a method using chromic acid, (2) a method using permanganic acid, or (3) a method using TEMPO reagent can be cited. The method using chromic acid or permanganic acid is carried out as described in *Comprehensive Organic Transformations*

(Richard C. Larock, VCH Publishers, Inc., (1989)). The method using TEMPO reagent is carried out as described before.

The compounds represented by formula (2) can be prepared by using conventionally known methods (for example, the method illustrated in reaction scheme described below), similar method, or methods described in Examples in this specification.

In each reaction in this description, the reaction product can be purified by general purification techniques, such as distillation under ordinary pressure or a reduced pressure, high performance liquid chromatography using silica gel or magnesium silicate, thin layer chromatography, column chromatography, washing, recrystallization and the like. Purification may be carried out for each reaction or after completion of several reactions.

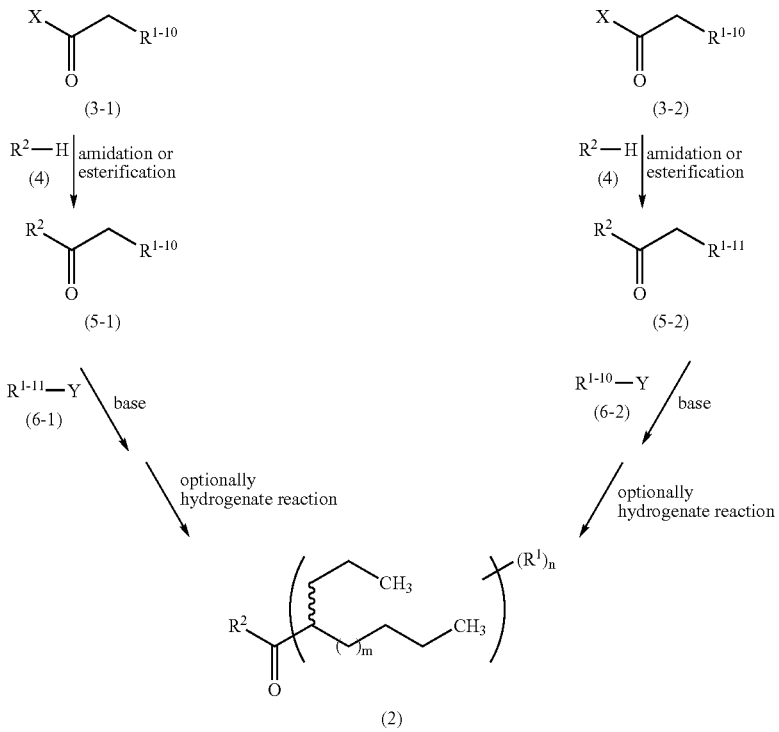

In the reaction scheme 1, $R^{1-10}$ represents propyl or propenyl which may substituted by 1 to 3 of optionally protected hydroxy, X represents hydroxy or halogen atom (e.g., chlorine atom, bromine atom, iodine atom, and the like), $R^{1-11}$ represents C3-13 alkyl or C3-13 alkenyl which may substituted by 1 to 3 of optionally protected hydroxy, Y represents leaving group (e.g., halogen atom (e.g., chlorine atom, bromine atom, iodine atom, and the like), p-toluenesulfonyloxy, trifluoromethanesulfonyloxy, methanesulfonyloxy, and the like), and other symbols have the same meanings as described above.

The compounds of formulae (3-1), (3-2), (4), (5-1), (5-2), (6-1), or (6-2) to be used as the starting materials or reagents are conventionally known by themselves or can be easily produced by using conventionally known methods or by using methods described in Examples in this specification.

The heating reaction in each reaction of the present invention may be performed using a water bath, an oil bath, a sand bath or a microwave, though it is apparent to those skilled in the art.

In each reaction of the present invention, polymer-supported reagent which is supported on macromolecule polymer (e.g., polystyrene, polyacrylamide, polypropylene, polyethylene glycols, and the like) can be used.

Application to Medicaments

The compound represented by formula (I) of the present invention, the salt thereof or the prodrug thereof is useful for a therapeutic agent for a neurodegenerative disease, cause it has an improving property of astrocyte function, an improving property of brain function and/or an inhibiting property of S100β expression. In addition, "the therapeutic agent" of the present invention means not only so-called "therapeutic agent" which leads the condition of the disease toward healing, but also so-called "agent for prevention of disease progression" which suppresses or keeps not to progress the progression of the disease.

In this case, the neurodegenerative diseases include all diseases which are accompanied by degeneration of nerve cells and are not limited by the cause of diseases. The neurodegenerative disease include neuropathy too. The nerve cells may be any type of nerve cells in vivo and, for example, they may be cells of central nerves (e.g., cranial nerves, spinal nerves) or peripheral nerves (e.g., of autonomic nerve system (such as sympathetic nerve and parasympathetic nerve)) and the like. The neurodegenerative diseases are desirably diseases of central nerves, and their examples include Parkinson's disease, Parkinson's syndrome, Alzheimer's disease, Down's disease, amyotrophic lateral sclerosis, familial amyotrophic lateral sclerosis, progressive supranuclear palsy, huntington's disease, spinocerebellar degeneration, dentatorubral-pallidoluysian atrophy, olivopontocerebellar atrophy, corticobasal degeneration, familial dementia, frontotemporal dementia, senile dementia, diffuse Lewy body disease, striato-nigral degeneration, chorea-athetosis, dystonia, Meige's syndrome, late cortical cerebellar atrophy, familial spastic paraplegia, motor neuron disease, Machado-Joseph disease, Pick's disease, moyamoya disease, stroke (e.g., brain hemorrhage (e.g., hypertensive intracerebral hemorrhage), brain infarction (e.g., cerebral thrombosis, cerebral embolism), transient ischemic attack, subarachnoidal hemorrhage), neuronal dysfunction by cerebrovascular disorder (e.g., brain hemorrhage, brain infarction, transient ischemic attack, subarachnoidal hemorrhage), neuronal dysfunction by cerebrospinal injury, demyelinating disease (e.g., multiple sclerosis, Guillain-Barre syndrome, acute disseminated encephalomyelitis, acute parencephalitis, transverse myelitis), brain tumor (e.g., strocytoma), cerebrospinal disease associated with infection (e.g., cerebral meningitis, cerebral abscess, Creutzfeldt-Jakob disease, AIDS dementia), psychiatric disorder (e.g., schizophrenia, circulatory psychosis, nervous disease, psychosomatic disorder, epilepsy) and the like. As the neurodegenerative disease, for example, stroke can be cited, more preferably. For example, brain infarction is most preferable and acute-phase brain infarction is especially preferable. Though it should not be interpreted strictly, acute-phase brain infarction means brain infarction within 2 weeks of after onset.

The term "neuropathy" as used herein includes all neurological dysfunctions. Examples of the neuropathy include transient blindness (e.g., transient amaurosis), disturbance of consciousness, hemiplegia, sensory disturbance, aphasia, alternate hemiplegia, two-side quadriplegia, homonymous hemianopsia, vertigo, ear noises, nystagmus, double vision, coma and the like. Preferably, neuropathies which accompanies previously-described neurodegenerative diseases can be cited.

When the compound of the present invention is used for the above-described purpose, generally, it is systemically or topically administered orally or parenterally.

Clinical dose varies dependent on the compound which is used for the present invention. And also, it varies dependent on the age, body weight, symptoms, therapeutic effect, administration method, treating period and the like, but in general, it is orally administered once or several times a day, within the range of 1 microgram to 1000 mg per once per one adult, or parenterally administered once or several times a day, within the range of 0.1 ng to 100 mg per once per one adult. The preferable method of parenterally administration is intravenous administration, so the administration is conducted continuously through a vein within the range of 1 hour to 24 hours a day.

Since the dose varies under various conditions as a matter of course as described in the foregoing, a smaller dose than the above range may be sufficient enough in some cases, or administration exceeding the above range may be necessary in some cases.

When a combination drug of the compound of the present invention represented by formula (I) and other drug is administered, it is used as solid compositions for internal use, liquid compositions for internal use, and injections, external preparations, suppositories, inhalations, preparations for nasal administration, and the like for parenteral administration.

Tablets, pills, capsules, powders, granules and the like are included in the solid compositions for internal use for use in the oral administration. Hard capsules and soft capsules are included in the capsules. Also, sublingual tablets, buccal adhesive tablets, buccal quick disintegration tablets and the like are included in the tablets.

In such solid compositions for internal use, one or more active substance(s) are directly used or after making into pharmaceutical preparations by the law of the art by mixing with an excipient (lactose, mannitol, glucose, microcrystalline cellulose, starch, etc.), a binder (hydroxypropylcellulose, polyvinylpyrrolidone, magnesium aluminometasilicate, etc.), a disintegrant (cellulose calcium glycolate, etc.), a lubricant (magnesium stearate, etc.), a stabilizing agent, a solubilizing agent (glutamic acid, aspartic acid, etc.) and the like. If necessary, they may be coated with a coating agent (sucrose, gelatin, hydroxypropylcellulose, hydroxypropylmethylcellulose phthalate, etc.), or coated with two or more layers. In addition, a capsule of an absorbable substance such as gelatin is also included therein.

The sublingual tablets are produced in accordance with a conventionally known method. For example, one, two or more active substance(s) are used after making into pharmaceutical preparations by the law of the art by mixing with an excipient (lactose, mannitol, glucose, microcrystalline cellulose, colloidal silica, starch, etc.), a binder (hydroxypropylcellulose, polyvinylpyrrolidone, magnesium aluminometasilicate, etc.), a disintegrant (starch, L-hydroxypropylcellulose, carboxymethylcellulose, croscarmellose sodium, cellulose calcium glycolate, etc.), a lubricant (magnesium stearate, etc.), a swelling agent (hydroxypropylcellulose, hydroxypropylmethylcellulose, carbopol, carboxymethylcellulose, polyvinyl alcohol, xanthan gum, guar gum, etc.), a swelling adjuvant (glucose, fructose, mannitol, xylitol, erythritol, maltose, trehalose, phosphate, citrate, silicate, glycine, glutamic acid, arginine, etc.), a stabilizing agent, a solubilizing agent (polyethylene glycol, propylene glycol, glutamic acid, aspartic acid, etc.), a flavoring agent (orange, strawberry, mint, lemon, vanilla, etc.) and the like. Also, if necessary, they may be coated with a coating agent (sucrose, gelatin, hydroxypropylcellulose, hydroxypropylmethylcellulose phthalate, etc.), or coated with two or more layers. In addition, if necessary, a preservative, an antioxidant, a colorant, a sweetening agent and the like generally used additive agents can also be added thereto.

The buccal adhesive tablets are produced in accordance with a conventionally known method. For example, one, two or more active substance(s) are used after making into pharmaceutical preparations by the law of the art by mixing with an excipient (lactose, mannitol, glucose, microcrystalline cellulose, colloidal silica, starch, etc.), a binder (hydroxypropylcellulose, polyvinylpyrrolidone, magnesium aluminometasilicate, etc.), a disintegrant (starch, L-hydroxypropylcellulose, carboxymethylcellulose, croscarmellose sodium, cellulose calcium glycolate, etc.), a lubricant (magnesium stearate, etc.), an adhesive agent (hydroxypropylcellulose, hydroxypropylmethylcellulose, carbopol, carboxymethylcellulose, polyvinyl alcohol, xanthan gum, guar gum, etc.), an adhesive adjuvant (glucose, fructose, mannitol, xylitol, erythritol, maltose, trehalose, phosphate, citrate, silicate, glycine, glutamic acid, arginine, etc.), a stabilizing agent, a solubilizing agent (polyethylene glycol, propylene glycol, glutamic acid, aspartic acid, etc.), a flavoring agent (orange, strawberry, mint, lemon, vanilla, etc.) and the like. Also, if necessary, they may be coated with a coating agent (sucrose, gelatin, hydroxypropylcellulose, hydroxypropylmethylcellulose phthalate, etc.), or coated with two or more layers. In addition, if necessary, a preservative, an antioxidant, a colorant, a sweetening agent and the like generally used additive agents can also be added thereto.

The buccal quick disintegration tablets are produced in accordance with a conventionally known method. For example, one, two or more active substance(s) are used as such or after making into pharmaceutical preparations by the law of the art by mixing the active substances, prepared by coating the material powder or granulated material particles with an appropriate coating agent (ethyl cellulose, hydroxypropylcellulose, hydroxypropylmethylcellulose, acrylate-methacrylate copolymer, etc.) and a plasticizer (polyethylene glycol, triethyl citrate, etc.), with an excipient (lactose, mannitol, glucose, microcrystalline cellulose, colloidal silica, starch, etc.), a binder (hydroxypropylcellulose, polyvinylpyrrolidone, magnesium aluminometasilicate, etc.), a disintegrant (starch, L-hydroxypropylcellulose, carboxymethylcellulose, croscarmellose sodium, cellulose calcium glycolate, etc.), a lubricant (magnesium stearate, etc.), a dispersing adjuvant (glucose, fructose, mannitol, xylitol, erythritol, maltose, trehalose, phosphate, citrate, silicate, glycine, glutamic acid, arginine, etc.), a stabilizing agent, a solubilizing agent (polyethylene glycol, propylene glycol, glutamic acid, aspartic acid, etc.), a flavoring agent (orange, strawberry, mint, lemon, vanilla, etc.) and the like. Also, if necessary, they may be coated with a coating agent (sucrose, gelatin, hydroxypropylcellulose, hydroxypropylmethylcellulose phthalate, etc.), or coated with two or more layers. In addition, if necessary, a preservative, an antioxidant, a colorant, a sweetening agent and the like generally used additive agents can also be added thereto.

The liquid compositions for internal use for use in oral administration includes pharmaceutically acceptable solutions, suspensions, emulsions, syrups, elixirs and the like. In such solutions, one or more active substance(s) are dissolved, suspended or emulsified in a generally used inert diluent (purified water, ethanol or a mixed liquid thereof. In addition, these liquid compositions may contain humectants, suspending agents emulsifying agents, sweetening agents, flavoring agents, aromas, preservatives, buffering agents and the like.

Dosage forms of the external preparations for parenteral administration include, for example, ointments, gels, creams, fomentations, adhesive preparations, liniments, air sprays, inhalations, sprays, aerosols, eye drops, nasal drops and the like. These contain one or more active substance(s) and are prepared by conventionally known methods or generally used recipes.

The ointments are prepared by conventionally known or generally used recipes. For example, these are produced and prepared by mixing or melting one or more active substance(s) in the base. The ointment base is selected from those which are conventionally known or generally used. For example, those which are selected from higher fatty acids or higher fatty acid esters (adipic acid, myristic acid, palmitic acid, stearic acid, oleic acid, adipic acid ester, myristic acid ester, palmitic acid ester, stearic acid ester, oleic acid ester, etc.), waxes (beeswax, spermaceti, ceresin, etc.), surfactants (polyoxyethylene alkyl ether phosphoric acid ester, etc.), higher alcohols (cetanol, stearyl alcohol, cetostearyl alcohol, etc.), silicon oils (dimethyl polysiloxane, etc.), hydrocarbons (hydrophilic petrolatum, white petrolatum, purified lanolin, liquid paraffin, etc.), glycols (ethylene glycol, diethylene glycol, propylene glycol, polyethylene glycol, macrogol, etc.), plant oils (castor oil, olive oil, sesame oil, turpentine oil, etc.), animal oils (minke whale oil, yolk oil, squalane, squalene, etc.), water, absorption accelerators and rash preventing agents are used alone or by mixing two or more thereof. In addition, these may contain a humectant, a preservative, a stabilizing agent, an antioxidant, a flavoring agent and the like.

The gels are prepared by conventionally known or generally used recipes. For example, these are prepared by melting one or more active substance(s) in a base. The gel base is selected from those which are conventionally known or generally used. For example, those which are selected from lower alcohols (ethanol, isopropyl alcohol, etc.), gelling agents (carboxymethylcellulose, hydroxyethylcellulose, hydroxypropylcellulose, ethylcellulose, etc.), neutralizing agents (triethanolamine, diisopropanolamine, etc.), surfactants (polyethylene glycol monostearate, etc.), gums, water, absorption accelerators and rash preventing agents are used alone or by mixing two or more thereof. In addition, these may contain a preservative, an antioxidant, a flavoring agent and the like.

The creams are prepared by conventionally known or generally used recipes. For example, these are prepared by melting or emulsifying one or more active substance(s) in a base. The cream base is selected from those which are conventionally known or generally used. For example, those which are selected from higher fatty acid esters, lower alcohols, hydrocarbons, polyhydric alcohols (propylene glycol, 1,3-butylene glycol, etc.), higher alcohols (2-hexyldecanol, cetanol, etc.), emulsifying agents (polyoxyethylene alkyl ethers, fatty acid esters, etc.), water, absorption accelerators and rash preventing agents are used alone or by mixing two or more thereof. In addition, these may contain a preservative, an antioxidant, a flavoring agent and the like.

The fomentations are prepared by conventionally known or generally used recipes. For example, these are prepared by melting one or more active substance(s) in a base, and spreading and coating the kneaded material on a support. The fomentation base is selected from those which are conventionally known or generally used. For example, those which are selected from viscosity-increasing agents (polyacrylic acid, polyvinylpyrrolidone, gum arabic, starch, gelatin, methylcellulose, etc.), humectants (urea, glycerol, propylene glycol, etc.), excipients (kaolin, zinc oxide, talc, calcium, magnesium, etc.), water, solution adjuvants, adhesiveness providing agents and rash preventing agents are used alone or by mixing two or more thereof. In addition, these may contain a preservative, an antioxidant, a flavoring agent and the like.

The adhesive preparations are prepared by conventionally known or generally used recipes. For example, these are prepared by melting one or more active substance(s) in a base, and spreading and coating this on a support. The base for adhesive preparations is selected from those which are conventionally known or generally used. For example, those which are selected from polymer bases, oils and fats, higher fatty acids, adhesiveness providing agents and rash preventing agents are used alone or by mixing two or more thereof. In addition, these may contain a preservative, an antioxidant, a flavoring agent and the like.

The liniments are prepared by conventionally known or generally used recipes. For example, these are prepared by dissolving, suspending or emulsifying one or more active substance(s) in one or two or more substance(s) selected from water, alcohols (ethanol, polyethylene glycol, etc.), higher fatty acids, glycerol, soap, emulsifying agents, suspending agents and the like. In addition, these may contain a preservative, an antioxidant, a flavoring agent and the like.

The air sprays, inhalations and sprays may contain a stabilizing agent such as sodium hydrogen sulfite and a buffering agent which provides tonicity, such as sodium chloride, sodium citrate, citric acid or the like tonicity agent, in addition to a generally used diluent. The production method of sprays are described in detail, for example, in U.S. Pat. No. 2,868,691 and U.S. Pat. No. 3,095,355.

As the injections for parenteral administration, solutions, suspensions, emulsions and solid injections which are used by dissolving or suspending in a solvent when used are included. The injections are used by dissolving, suspending or emulsifying one or more active substance(s) in a solvent. As the solvent, for example, distilled water for injection, physiological saline, plant oil, propylene glycol, polyethylene glycol, alcohol such as ethanol and a combination thereof are used. These injections may further contain a stabilizing agent, a solubilizing adjuvant (glutamic acid, aspartic acid, polysorbate 80 (trade name), etc.), a suspending agent, an emulsifying agent, a soothing agent, buffering agent, a preservative and the like. These are prepared by sterilizing in the final process or by a sterile operation method. Alternatively, they may be used by firstly producing sterile solid preparations such as freeze-dried preparations and dissolving them in sterilized or sterile distilled water or other solvent for injection prior to their use.

As the inhalations for parenteral administration use, aerosols, powders for inhalation use or solutions for inhalation use are included, and said solutions for inhalation use may be in such a form that they are used by dissolving or suspending in water or other appropriate medium prior to use.

These inhalations are produced in accordance with a conventionally known method.

For example, in the case of solutions for inhalation use, they are prepared by optionally selecting a preservative (benzalkonium chloride, paraben, etc.), a colorant, a buffering agent (sodium phosphate, sodium acetate, etc.), a tonicity agent (sodium chloride, concentrated glycerol, etc.), a viscosity-increasing agent (carboxy vinyl polymer, etc.), an absorption accelerating agent and the like, if necessary.

In the case of powders for inhalation use, they are prepared by optionally selecting a lubricant (stearic acid and a salt thereof, etc.), a binder (starch, dextrin, etc.), an excipient (lactose, cellulose, etc.), a colorant, a preservative (benzalkonium chloride, paraben, etc.), an absorption accelerating agent and the like, if necessary.

When solutions for inhalation use are administered, a sprayer (atomizer or nebulizer) is generally used, and an inhalation administration device for powder preparation use is generally used when powders for inhalation is used.

As other compositions for parenteral administration use, suppositories for rectal administration, pessaries for vaginal administration and the like, which contain one mo more active substance(s) and are formulated in the usual way, are included.

The compound represented by formula (I) the salt thereof, or the prodrug thereof (hereinafter, they will be abbreviated to "the inventive compound", simply) may be administered as a combination drug in combination with other drug for the purpose of (1) complementing and/or reinforcing preventive and/or therapeutic effect of the compound, (2) improving dynamics and absorption of the compound and reducing the dose, and/or (3) reducing side effects of the compound.

In addition, for the purpose of (1) complementing and/or reinforcing preventive and/or therapeutic effect, (2) improving dynamics and absorption, and/or (3) reducing side effects, of the other drug to be jointly used, it may be administered as a combination drug in combination with the compound of the present invention.

The combination drug of the inventive compound with other drug (hereinafter, it will be abbreviated to "the combination drug of the present invention") may be administered in the form of a combination drug in which both components are formulated in one pharmaceutical preparation, or in another form in which they are administered as separate preparations.

When administered as separate preparations, simultaneous administration and differential time administration are included. In addition, in the case of the differential time administration, "the inventive compound" may be firstly administered followed by the administration of the other drug, or the other drug may be firstly administered followed by the administration of "the inventive compound", and respective administration methods may be the same or different.

The diseases in which their preventive and/or therapeutic effects are exerted by the above-described combination drug are not particularly limited, and they may be the diseases in which preventive and/or therapeutic effect of the combination drug is complemented and/or reinforced.

As examples of the other drug to be used in the combination drug of the present invention, for example, acetylcholine esterase inhibitors, nicotinic receptor regulators, production, secretion, accumulation, aggregation and/or deposition inhibitors of β-amyloid (e.g., β-secretase inhibitors, gamma-secretase inhibitors, β-amyloid protein aggregation inhibitors, β-amyloid vaccines, β-amyloid proteases, and the like), brain function activators, improvers of brain circulation and metabolism, other curative medicines of Parkinson's disease (e.g., dopamine receptor agonists, monoamine oxidase (MAO) inhibitors, anticholinergic drugs, catechol-O-methyl-transferase (COMT) inhibitors, and the like), curative medicines of amyotrophic lateral sclerosis, neurotrophic factors, curative medicines of abnormal behavior, prowl, and the like accompanied to progression of dementia, apoptosis inhibitor, differentiation/regeneration accelerators of nerve cells, antidepressants, antianxiety drugs, antiepileptic drugs, hypotensive drugs, calcium receptor antagonists, curative medicine of diabetes, curative medicines of hyperlipimedia such as cholesterol-lowering agents (e.g., statins, fibrates, squalene synthase inhibitors, and the like), aldose reductase inhibitors, nonsteroidal anti-inflammatory drugs, disease modifying antirheumatic drugs, anticytokines (e.g., TNF inhibitor, MAP kinase inhibitor, and the like), steroids, sex hormones or derivatives thereof, parathyroid hormone (e.g., PTH), factor Xa inhibitor, factor VIIa inhibitor, antioxidant drugs, glycerites, and the like can be cited.

Examples of acetylcholine esterase inhibitors include, for example, donepezil hydrochloride, rivastigmine, galantamine, zanapezil (TAK-147) and the like.

Examples of β-secretase inhibitors include, for example,
6-(4-biphenylyl)methoxy-2-[2-(N,N-dimethylamino)ethyl]tetralin,
6-(4-biphenylyl)methoxy-2-(N,N-dimethylamino)methyltetralin,
6-(4-biphenylyl)methoxy-2-(N,N-dipropylamino)methyltetralin,
2-(N,N-dimethylamino)methyl-6-(4'-methoxybiphenyl-4-yl)methoxytetralin,
6-(4-biphenylyl)methoxy-2-[2-(N,N-diethylamino)ethyl]tetralin,
2-[2-(N,N-dimethylamino)ethyl]-6-(4'-methylbiphenyl-4-yl)methoxytetralin,
2-[2-(N,N-dimethylamino)ethyl]-6-(4'-methoxybiphenyl-4-yl)methoxytetralin,
6-(2',4'-dimethoxybiphenyl-4-yl)methoxy-2-[2-(N,N-dimethylamino)ethyl]tetralin,
6-[4-(1,3-benzodioxol-5-yl)phenyl]methoxy-2-[2-(N,N-dimethylamino)ethyl]tetralin,
6-(3',4'-dimethoxybiphenyl-4-yl)methoxy-2-[2-(N,N-dimethylamino)ethyl]tetralin, optically active substance thereof, salts thereof and hydrates thereof, OM99-2 (WO01/00663) and the like.

Examples of β-amyloid protein aggregation inhibitors include, for example, PTI-00703, ALZHEMED (NC-531), PPI-368 (JP-A-11-514333), PPI-558 (JP-A-2001-500852), SKF-74652 (*BIOCHEM J.*, 340(1), 283-289, 1999) and the like.

Examples of brain function activators include, for example, aniracetam, nicergoline and the like.

Examples of improvers of brain circulation and metabolism include, for example, idebenone, hopantenic acid calcium, amantadine hydrochloride, meclofenoxate hydrochloride, dihydroergotoxine mesilate, pyritioxine hydrochloride, gamma-aminobutyric acid, bifemelane hydrochloride, lisuride malate, indeloxazine hydrochloride, nicergoline, propentofylline and the like.

Examples of dopamine receptor agonists include, for example, L-dopa, bromocriptine, pergolide, talipexole, pramipexole, cabergoline, amantadine and the like.

Examples of monoamine oxidase (MAO) inhibitors include, for example, safrazine, deprenyl, selegiline, remacemide, riluzole and the like.

Examples of anticholinergic drugs include, for example, trihexyphenidyl, biperiden and the like.

Examples of catechol-O-methyltransferase (COMT) inhibitors include, for example, entacapone and the like.

Examples of curative medicines of amyotrophic lateral sclerosis include, for example, riluzole, neurotrophic factor (e.g., ABS-205) and the like.

Examples of apoptosis inhibitor include, for example, CPI-1189, IDN-6556 CEP-1347 and the like.

Examples of differentiation/regeneration accelerators of nerve cells include, for example, leteprinim, xaliproden (SR-57746-A), SB-216763 and the like.

Examples of antiepileptic drugs include, for example, phenobarbital, mephobarbital, metharbital, primidone, phenytoin, ethotoin, trimethadione, ethosuximide, acetylphenetuuride, carbamazepine, acetazolamide, diazepam, sodium valproate and the like.

Examples of statins of curative medicines of hyperlipidemia include, for example, pravastatin sodium, atrovastatine, simvastatin, rosuvastatin and the like.

Examples of fibrates of curative medicines of hyperlipidemia include, for example, clofibrate and the like.

Examples of nonsteroidal anti-inflammatory drugs include, for example, meloxicam, tenoxicam, indometacin, ibuprofen, celecoxib, rofecoxib, aspirin and the like.

Examples of steroids include, for example,dexamethasone, hexestrol, cortisone acetate and the like.

Examples of sex hormones or derivatives thereof include, for example, progesteron, estradiol, estradiol benzoate and the like.

Examples of antioxidant drugs include, for example, edaravone and the like.

Examples of glycerites include, for example, glyceol and the like.

The drugs described hereinbefore is merely example, so the combination drug of the present invention does not limited thereto.

For a clinical dose and an administration method of "the compound of the present invention", the method same as described before can be used.

Mass ratio of "the compound of the present invention" and other drug is not particularly limited. The other drug may be administered as a combination of optional two or more species. In addition, not only those which have so far been found but also will be found based on the above-described mechanism are included in the other drug which complement and/or reinforce the preventive and/or therapeutic effect of "the compound of the present invention".

Also, in combination with antithrombotic drugs (include thrombolytic agents), "the compound of the present invention" is useful for treating brain infarction. It can improve survival rate of patients or neurologic symptoms synergistically, without inhibition of thrombolytic effect of antithrombotic drugs. Examples of antithrombotic drugs include, for example, tissue plasminogen activator (e.g., t-PA, alteplase), urobilinogen, urokinase, tisokinase, heparin, oral anticoagulants (e.g., warfarin), synthetic thrombin inhibitors (e.g., gabexate mesilate, nafamostat mesilate, argatroban), platelet inhibitor (e.g., aspirin, dipyridamole, ticlopidine hydrochloride, beraprost sodium, cilostazol, ozagrel sodium) and the like. More preferably, tissue plasminogen activator or warfarin can be cited. Brain infarction includes brain hemorrhage, subarachnoid hemorrhage, leukodystrophy.

Toxicity

Toxicity of the compound of the present invention represented by formula (I) is sufficiently low, so it was confirmed to be safe enough for use as pharmaceuticals.

Effect of the Present Invention

The compounds of the present invention represented by formula (I) are useful for curative medicine of neurodegenerative diseases, cause they are improved in physico-chemical property such as intraoral acridity, free of side effect, and which have an improving effect of astrocyte function, an improving effect of brain function, and/or an inhibitory effect of S100β expression.

It can be confirmed by the method described hereinafter, that the compounds of the present invention represented by formula (I), salts thereof or prodrugs thereof show the effect described in this specification.

(1) It can be confirmed by the method described in the specification of EP0632008, especially in Example 1, that they have an improving effect of astrocyte function.

(2) It can be confirmed by the method described in the specification of EP0632008, especially in Example 2, that they have an ability to recover the GABAA receptor response in reactive astrocytes.

(3) It can be confirmed by the method described in the specification of EP0632008, especially in Example 3, that they have an ability to inhibit neuronal death in neurocyte-astrocyte co-culture.

(4) It can be confirmed by the method described in the specification of EP0632008, especially in Example 4, that they have an ability to improve disability in active avoidance learning induced by brain ischemic-reperfusion injury.

(5) It can be confirmed by the method described in the specification of EP1174131, especially in Example 1, that they are effective in experimental animal model of Parkinson's disease induced by MPTP.

(6) It can be confirmed by the method described in this specification, especially in Example described hereinafter, that they have an ability to reduce the intracellular content of S100β.

(7) It can be confirmed by gustatory test of human or observation of behavior of mouse to which the compound was injected intraperitoneally, that they are improved in acridity.

(8) It can be confirmed by the method described in this specification, especially in Example described hereinafter, that they are free of side effect.

And also, it can be confirmed by the method of thrombin-induced local brain ischemic model described in the specification of WO03/007992, especially in Example 1, that the combination of the compound of the present invention represented by formula (I), a salt thereof, or a prodrug thereof and an thrombolytic drug is effective to result described in this specification.

BEST MODE FOR CARRYING OUT THE INVENTION

The following Examples are provided to illustrate the present invention in detail, but are not to be constructed as limiting the invention.

The solvents in the parenthesis described in chromatography separation and TLC show an elution solvent or a developing solvent used, and the ratio is given in volume.

The solvents in the parenthesis described in NMR show an solvent for measurement, if unspecified, $CDCl_3$ was used.

Mechanical IUPAC nomenclature of the compounds described in this specification was performed using a computer program ACD/NAME Batch (TRADE NAME: available from Advanced Chemistry Development Co.) or performed manually with method based on IUPAC rule.

PREPARATION EXAMPLE

Reference Example 1

(4S)-N-pentanoyl-4-isopropyl-2-oxazolidinone

Under an atmosphere of nitrogen, to a mixed solution of tetrahydrofuran (383 ml) (hereinafter, abbreviated as THF) and triethylamine (88 ml) was added valeric acid (38 g) and dissolved. To the mixture was dropped pivaloyl chloride (45 ml) at −15° C. to −10° C. The reaction mixture was stirred at −10° C. for 1 hour, and thereto was added anhydrous lithium chloride (12 g). To the mixture was added a solution of (S)-4-isopropyl-2-oxazolidinone (32.3 g) in THF (118 ml), and the reaction mixture was stirred at 25° C. for 15 hours. To the mixture were added an saturated aqueous solution of sodium carbonate and water, and the mixture was stirred for 18 hours. To the reaction mixture were added water, a mixed solvent (n-heptane:ethyl acetate=2:1) (300 ml) and aqueous solution of sodium hydroxide (2 N) (100 ml), and the mixture was extracted. The aqueous layer was extracted with a mixed solvent (n-heptane:ethyl acetate=2:1). The combined organic layer was washed with water, hydrochloric acid (3 N), water, an saturated aqueous solution of sodium bicarbonate, and brine sequentially. The obtained organic layer was dried over anhydrous magnesium sulfate, and filtrated and concentrated to give the title compound (51.5 g) having the following physical data.

TLC: Rf 0.55 (n-hexane:ethyl acetate=5:1);

NMR: δ 4.50-4.40 (m, 1H), 4.30-4.10 (m, 2H), 3.10-2.80 (m, 2H), 2.50-2.30 (m, 1H), 1.75-1.60 (m, 2H), 1.50-1.45 (m, 2H), 1.00-0.85 (m, 9H).

Reference Example 2

(4S)-N-[(2R)-2-propyl-7-octenoyl]-4-isopropyl-2-oxazolidinone

Under an atmosphere of nitrogen, to a solution of the compound prepared in Reference Example 1 (21.5 g) in THF (20 ml) were added 1,3-dimethyl-3,4,5,6-tetrahydro-2(1H)-pyrimidinone (36.5 ml), 6-iodo-1-hexene (31.5 g). To the solution was dropped lithium diisopropylamine (2 mol/L (dissolved in 55 ml of heptane:THF:ethylbenzene)) at −60° C., and stirred at 115° C. for 17 hours. The reaction mixture was poured into saturated aqueous solution of ammonium chloride, and thereto were added water and a mixed solvent (n-heptane:ethyl acetate=2:1), and the mixture was extracted. The aqueous layer was extracted with a mixed solvent (n-heptane:ethyl acetate=2:1). The combined organic layer was washed with brine and concentrated. The obtained residue was purified by column chromatography on silica gel (n-hexane:ethyl acetate=125:10→10:1) to give the title compound (20 g) having the following physical data.

TLC: Rf 0.53 (n-hexane:ethyl acetate=2:1);

NMR: δ 5.95-5.80 (m, 1H), 5.05-4.90 (m, 2H), 4.50-4.40 (m, 1H), 4.30-4.15 (m, 2H), 3.90-3.80 (m, 1H), 2.50-2.30 (m, 1H), 2.10-2.00 (m, 2H), 1.80-1.60 (m, 2H), 1.60-1.20 (m, 8H), 1.00-0.80 (m, 9H).

Reference Example 3

(4S)-N-[(2R)-7-oxo-2-propyloctanoyl]-4-isopropyl-2-oxazolidinone

To a solution of the compound prepared in Reference Example 2 (39.6 g) in a mixed solvent of N,N-dimethylamide (200 ml) and water (26 ml) were added palladium chloride (2.4 g) and copper (II) acetate hydrate (5.2 g). Under an atmosphere of oxygen, the mixture was stirred at 25° C. for 24 hours. To the reaction mixture were added water and a mixed solvent (n-heptane:ethyl acetate=2:1) and the mixture was stirred for 30 minutes. The precipitated solid was filtrated and washed with a mixed solvent (n-heptane:ethyl acetate=2:1). The filtrate was separated to an organic layer and an aqueous layer. To the aqueous layer was added a mixed solvent (n-heptane:ethyl acetate=2:1) and the mixture was extracted. The combined organic layer was washed with brine. The obtained organic layer was dried over anhydrous magnesium sulfate, and filtrated and concentrated. The obtained residue was purified by column chromatography on silica gel (n-hexane:ethyl acetate=6:1→5:1) to give the title compound (31 g) having the following physical data.

TLC: Rf 0.42 (n-hexane:ethyl acetate=2:1);

NMR: δ 4.50-4.45 (m, 1H), 4.30-4.20 (m, 2H), 3.90-3.80 (m, 1H), 2.50-2.30 (m, 3H), 2.12 (s, 3H), 1.80-1.20 (m, 10H), 1.00-0.80 (m, 9H).

Reference Example 4

(4S)-N-[(2R)-8-hydroxy-2-propyloctanoyl]-4-isopropyl-2-oxazolidinone

Under an atmosphere of nitrogen, to a solution of the compound prepared in Reference Example 2 (2.95 g) in THF (10 ml) was dropped 9-borabicyclo[3.3.1]nonane (0.5 mol/L, dissolved in THF, 30 ml). The reaction mixture was stirred at 25° C. for 2 hours. To the reaction mixture was added an aqueous solution of sodium bicarbonate (4.2 g) at 3° C., and thereto was dropped a hydrogen peroxide solution (30%, 5.7 ml). The reaction mixture was stirred at 25° C. for 17 hours, and thereto were added water and ethyl acetate, and the mixture was extracted. To the aqueous layer was added ethyl acetate and the mixture, and the mixture was extracted. The combined organic layer was washed with saturated aqueous solution of sodium sulfite and brine, and dried over anhydrous magnesium sulfate, and filtrated and concentrated. The obtained residue was purified by column chromatography on silica gel (n-hexane:ethyl acetate=2:1) to give the title compound (2.75 g) having the following physical data.

TLC: Rf 0.20 (n-hexane:ethyl acetate=2:1);

NMR: δ 4.50-4.45 (m, 1H), 4.30-4.20 (m, 2H), 3.90-3.80 (m, 1H), 3.70-3.60 (m, 2H), 2.45-2.35 (m, 1H), 1.80-1.20 (m, 14H), 0.95-0.85 (m, 9H).

Reference Example 5

(4R)-N-[(2R,7S)-7-hydroxy-2-propyloctanoyl]-4-isopropyl-2-oxazolidinone

The title compound (34 g) having the following physical data was obtained by the following procedure (1)-(4).
(1) the same procedure as described in Reference Example 1 using (7S)-7-[t-butyldiphenylsilyloxy]-5-octenoic acid instead of valeric acid,
(2) the same procedure as described in Reference Example 2 using aryl bromide instead of 6-iodo-1-hexen,
(3) the deprotection reaction of silyl group using hydrochloric acid (2 N), and then
(4) the hydrogenate reaction using 5% platinum-carbon.
TLC: Rf 0.40 (n-hexane:ethyl acetate=4:1);
NMR: δ 4.49-4.45 (m, 1H), 4.26 (t, J=8.8 Hz, 1H), 4.19 (dd, J=10.4, 3.2 Hz, 1H), 3.87-3.81 (m, 1H), 3.79-3.74 (m, 1H), 2.45-2.32 (m, 1H), 1.74-1.63 (m, 2H1), 1.52-1.24 (m, 11H), 1.17 (d, J=6.0 Hz, 3H), 0.93-0.87 (m, 9H).

Reference Example 6

(4R)-N-[(2R,7R)-7-formyloxy-2-propyloctanoyl]-4-isopropyl-2-oxazolidinone

Under an atmosphere of argon, to a solution of the compound prepared in Reference Example 5 (40.0 g) in THF (500 ml) were added triphenylphosphine (40.2 g), formic acid (9.0 g), and finally, thereto was dropped diisopropylazodicarboxylate (77.4 g) and the mixture was stirred at room temperature for 1 hour. Reaction mixture was concentrated and the obtained residue was purified by column chromatography on silica gel (n-hexane:ethyl acetate=1:1, silica gel for flash chromatography) to give the title compound (29.4 g) having the following physical data.
NMR: δ 8.03 (s, 1H), 5.05-4.96 (m, 1H), 4.47 (dt, J=8.8, 2.8 Hz, 1H), 4.27 (t, J=8.8 Hz, 1H), 4.19 (dd, J=9.2, 3.2 Hz, 1H), 3.87-3.80 (m, 1H), 2.40-2.32 (m, 1H), 1.74-1.26 (m, 12H), 1.24 (d, J=3.2 Hz, 3H), 0.93-0.87 (m, 9H).

Example 1(1)

(2R)-7-oxo-2-propyloctanoic acid

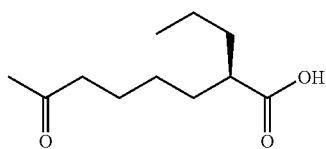

To a solution of the compound prepared in Reference Example 3 (31 g) in a mixed solvent of THF (310 ml) and water (31 ml) was added a hydrogen peroxide solution (30%, 45.3 ml) at 6° C., and thereto was dropped an aqueous solution of lithium hydroxide (2 mol/L, 100 ml) at 5° C. The reaction mixture was stirred at 26° C. for 1 hour, and thereto was added methylene chloride to extract. To the aqueous layer was added hydrochloric acid (6 N) on ice bath to adjust pH is 2.0, and extracted with ethyl acetate. The extract was washed with water and brine sequentially and concentrated. The obtained residue was purified by column chromatography on silica gel (n-hexane:ethyl acetate=2:1) to give the compound of the present invention (17.3 g) having the following physical data.
TLC: Rf 0.54 (chloroform:methanol:acetic acid=30:3:1);
NMR: δ 0.91 (t, J=7.05 Hz, 3H), 1.48 (m, 10H), 2.13 (s, 3H), 2.40 (m, 1H), 2.43 (t, J=7.14 Hz, 2H).

Example 1(2)

(2R,7R)-7-hydroxy-2-propyloctanoic acid

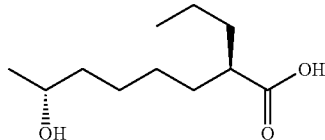

By the same procedure as described in Example 1(1) using the compound prepared in Reference Example 6 (29.4 g), the compound of the present invention (12.5 g) having the following physical data was obtained.
TLC: Rf 0.29 (methanol:dichloroethane=5:95);
NMR: δ 3.79 (1H, m), 2.38 (1H, m), 1.76-1.23 (12H, m), 1.19 (3H, d, J=6.4 Hz), 0.92 (3H, t, J=7 Hz).

Example 1(3)

(2R,7S)-7-hydroxy-2-propyloctanoic acid

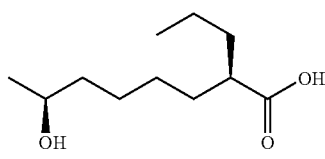

By the same procedure as described in Example 1(1) using the compound prepared in Reference Example 5 (40.0 g), the compound of the present invention (13.5 g) having the following physical data was obtained.
TLC: Rf 0.25 (n-hexane:ethyl acetate=1:1);
NMR: δ 0.92 (t, J=7.23 Hz, 3H), 1.18 (d, J=6.23 Hz, 3H), 1.40 (m, 10H), 1.63 (m, 2H), 2.37 (m, 1H), 3.80 (m, 1H).

Example 1(4)

(2R)-8-hydroxy-2-propyloctanoic acid

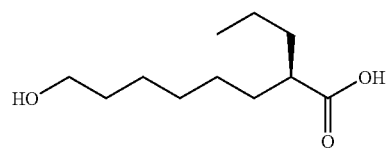

By the same procedure as described in Example 1(1) using the compound prepared in Reference Example 4 (2 g), the compound of the present invention (750 mg) having the following physical data was obtained.
TLC: Rf 0.45 (chloroform:methanol:acetic acid=30:3:1);
NMR: δ 0.91 (t, J=7.05 Hz, 3H), 1.50 (m, 14H), 2.37 (m, 1H), 3.64 (t, J=6.50 Hz, 2H).

Example 1(5)

(2R)-2-propylsuberic acid

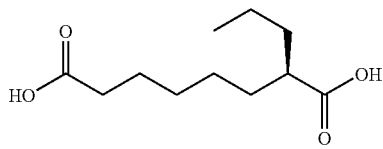

To a solution of the compound prepared in Example 1(4) (2.02 g) in acetonitrile (16 ml) was added 2,2,6,6-tetramethyl-1-piperidinyloxy (156 mg) at 35° C., and an aqueous solution of sodium chlorite (2.26 g of sodium chlorite was dissolved in 9 ml of water) (2 ml). To the solution was added slowly an aqueous solution of sodium chlorite (447 mg of sodium chlorite was dissolved in 4.5 ml of water). Moreover, to the solution was dropped residual aqueous solution of sodium chlorite. The reaction mixture was stirred at 35° C. for 5.5 hours. The reaction mixture was cooled and thereto was added water at room temperature. To the reaction mixture was added an aqueous sodium hydroxide (2 N) to adjust pH is 9, then the mixture was cooled and thereto was added an aqueous sodium sulfite (3.2 g of sodium sulfite was dissolved in 12 ml of water). The mixture was stirred at room temperature for 30 minutes, and was extracted with methyl-t-butylether. The aqueous layer was cooled on ice bath, then thereto was added hydrochloric acid to adjust pH is 2.0, and the mixture was extracted with methyl t-butyl ether. The combined organic layer was washed with brine, and dried over anhydrous magnesium sulfate, and filtrated and concentrated. The obtained residue was purified by column chromatography on silica gel (n-hexane:ethyl acetate=1:1→1:2) to give the compound of the present invention (2.11 g) having the following physical data.

TLC: Rf 0.37 (chloroform:methanol=10:1);

NMR: δ 2.35 (t, J=7 Hz, 2H), 2.45-2.30 (m, 1H), 1.75-1.25 (m, 12H), 0.90 (t, J=7 Hz, 3H).

Example 1(6)

(3 S)-3-hexyl-5-methyldihydrofuran-2(3H)-one

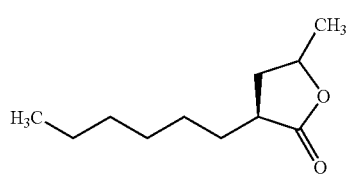

Under an atmosphere of argon, ethanol solution of (2S)-2-hexylpent-4-ynoic acid was reacted in the presence of palladium-calcium carbonate to give (3S)-3-hexyl-5-methylidenedihydrofuran-2-(3H)-one. The obtained compound was reacted in the presence of 5% palladium-carbon, under an atmosphere of hydrogen gas, to give the compound of the present invention having the following physical data.

TLC: Rf 0.28 (hexane:ethyle acetate:acetic acid=20:4:1);

NMR: δ 4.75-4.38 (m, 1H), 2.70-2.38 (m, 2H), 2.10-1.75 (m, 1H), 1.42 (d, J=7 Hz, 3H), 0.88 (t, J=7 Hz, 3H).

Example 1(7)

Sodium (2S)-2-(2-hydroxypropyl)octanoate

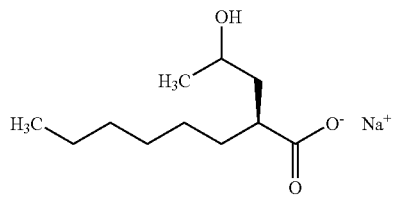

To an ethanol solution of the compound prepared in Example 1(6) was added an equivalent of an aqueous solution of sodium hydroxide, and the mixture was stirred at 75° C. for 3 hours. The reaction mixture was concentrated to give the compound of the present invention having the following physical data.

NMR (CD$_3$OD): δ 0.88 (t, J=6.59 Hz, 3 H), 1.12 and 1.15 (d, J=6.2 Hz, 3 H), 1.34 (m, 10 H), 1.55 (m, 1 H), 1.73 (m, 1 H), 2.32 (m, 1 H), 3.77 (m, 1 H).

Pharmacological Example

Example 2

The 1 to 2 day-old neonatal Wistar rats (10 animals) were decapitated and sterilized their heads in ethanol. Ethanol and blood was removed in ice-cold DMEM medium (purchased from Sigma). Meningis was peeled and cortex of cerebrum was removed in ice-cold DMEM medium (purchased from Sigma) under the stereomicroscope. The cortex of cerebrum was minced with frosted glass-slides (purchased from Matsunami) to suspension in ice-cold DMEM medium (purchased from Sigma). Cell suspension was filtrated with 70 micrometer-diameter filter (falcon2350). The filtrate was centrifuged at 100×g for 3 minutes, and the pellet was re-suspended in 10% FCS (fetal calf serum)-containing DMEM medium. The washing procedure using 10% FCS-DMEM medium was repeated 3 times and cells were re-suspended in 10% FCS-DMEM medium. The obtained cell suspension was plated in 75 cm$^2$ flask (falcon3024) (one flask (containing 12 ml of medium) containing cells obtained from one neonatal rat), and cultured at 37° C. under an atmosphere of 5% CO$_2$, 95% air (0 day of culture). After 2 days of culture (2 days of culture), culture media was aspirated and flask was shaken by hands to remove an unadhesive cells. The flask was washed with DMEM medium and the suspended cells ware removed. This procedure was repeated 3 times till the unadhesive cells were removed completely confirmed by microscope. Then, 10% FCS-DMEM medium was added to flask (12 ml/flask) and cultured at 37° C. under an atmosphere of 5% CO$_2$, 95% air (medium was changed in 12 days after onset of culture).

Example 3

Primary culture of Astrocytes (19 days after onset of culture, 3 flasks) was purified by the same procedure as used in cell purification in primary culture. Then, the adhesive cells were treated with 0.05% Trypsin-1 mmol/L EDTA at 37° C. till the cells were detached. The cells were suspended in 10%

FCS-DMEM medium and transferred to microtube. After centrifugation at 100×g for 3 minutes, the pellet was resuspended in 10% FCS-DMEM medium. A portion of cell suspension was mixed with an equal volume of Trypan-Blue solution. The number of living cells was measured by using the Burker-Turk counting chamber under the phase-contrast microscope. Cells were suspended in 10% FCS-DMEM medium at the cell density of $2 \times 10^5$ cells/ml and cultured in 48 well culture plate (6 plates, 0.5 ml/well) at 37° C. under an atmosphere of 5% $CO_2$, 95% air. After 24 hour cultivation, culture medium was changed to the test-compound containing medium (0.5 ml/well), and the cultivation was conducted for 2 weeks at 37° C. under an atmosphere of 5% $CO_2$, 95% air. The change of medium was conducted on 27 days after onset of cultivation.

Example 4

On 34 days after onset of cultivation, the culture supernatant of secondary cultured astrocytes which treated with test-compound prepared in Example 3 was removed and the cells was washed twice with ice-cold PBS. After addition of 100 microliter of Tris-SDS buffer (50 mmo/L Tris, 2 mmol/L EDTA-2Na, 0.15% SDS), the cells were lysed with shaking by shaker or pipetting to give the S100β containing sample. The obtained sample was reserved on ice till the measuring.

The measurement of S100β content in prepared sample was carried out by ELISA method using anti-S100β antibody. Anti-S100β antibody (β subunit) (purchased from Sigma, diluted to 1/1000 with 0.1 mol/L $Na_2CO_3$ (pH 9.6), 50 microliter/well) was added to each well of 96 well plate and the plate was stored overnight at 4° C. The plate was washed 4 times with Ca-TPBS (PBS which containing 1 mmol/L $CaCl_2$, 0.05% Tween 20), and blocking solution (200 microliter/well) was added, and the plate was stored for 4 hours at room temperature. After washing with Ca-TPBS, 50 microliter of sample (a solution which was prepared from S100β containing sample by diluting with 2% BSA-Ca-TPBS solution) or S100β standard (a solution (0.01-300 ng/ml) which was prepared from blocking/stock solution by diluting with 2% BSA-Ca-TPBS solution) was added to each well, and the plate was stored overnight at 4° C. After washing with Ca-TPBS, Anti-S100β antibody (purchased from DAKO, diluted to 1/1000 with 2% BSA-Ca-TPBS, 50 microliter/well) was added and the plate was stored for 2 hours at room temperature. After washing with Ca-TPBS, Horseradish peroxidase (HRP) conjugated anti-Rabbit IgG (purchased from Bio-Rad, diluted to 1/2000 with 2% BSA-Ca-TPBS, 50 microliter/well) was added and the plate was stored for 2 hours at room temperature. After washing Ca-TPBS, color developing reaction was carried out by using Peroxidase substrate kit (purchased from Bio-Rad, solution A was mixed with solution B at the ration of 9:1, 100 microliter/well). The reaction was stopped by addition of 2% aqueous oxalic acid solution (100 microliter/well), and the absorbance at 412 nm was measured. The S100β content in prepared sample was determined from the standard curve of S100β standard. The obtained data was represented as S100β content (ng) per unit protein (mg).

Quantitative determination of total protein was carried out by using BCA protein assay kit (purchased from PIERCE). 25 microliter of sample for measuring S100β content, standard for measuring total protein, or Tris-SDS buffer was transferred to 96 well plate. Then, 200 microliter of WR solution (solution A was mixed with solution B at the ration of 50:1) was added and the plate was shaken by shaker for 30 seconds. The plate was incubated for 30 minutes at 37° C. The absorbance at 562 nm was measured at the room temperature. Bovine serum albumin attached to the package was used as standard for measuring total protein, the total protein was determined from the standard curve.

The compound of Example 1(1) reduced intracellular content of S100β to 1489.0±37.84 (30 micromol/L-treated group (n=4)) or 1053.5±39.57 (100 micromol/L-treated group) from 2177.0±147.74 ng/mg unit protein (control group) with statistically significance (P<0.001; Statistically significance (Dunnett test) against control group). Moreover, the compound of Example 1(2) or Example 1(4) reduced intracellular content of S100β to 1422.5±74.70 (100 micromol/L-treated group) or 1192.8±58.78 (100 micromol/L-treated group), respectively. These results indicate that the compounds of the present invention have an ability to improve the functions of astrocyte.

Example 5

Each test compounds were dissolved with an aqueous solution of trisodium phosphate, and diluted with a water for injection. The obtained drug solution was orally administrated once daily to 6 weeks-old male rat by long-term repetitive dosing at a dose of 250 mg/kg per once. In result, the each groups which was administered compound prepared in Example 1(1) and Example 1(4) does not show a general side effect.

Formulation Examples

Example 6

Tablet:
(2R)-7-oxo-2-propyloctanoic acid sodium salt (converted from the compound prepared in Example 1(1) by conventional means, 100 kg), cellulose calcium glycolate (disintegrant, 2 kg), magnesium stearate (lubricant, 1 kg) and microcrystalline cellulose (97 kg) were admixed by conventional method, punched out to give 1 million tablets each containing 100 mg of active ingredient.

Example 7

Injectable Solution (1):
(2R)-7-oxo-2-propyloctanoic acid (20 kg), mannitol (200 kg) and distilled water (5 kl) were admixed by conventional method, filtrated with dust filter, dispensed in 5 ml portions into ampoules and then subjected to heat sterilization by autoclave, thereby obtaining 1 million ampoules each containing 20 mg of active ingredient.

Example 8

Soft Capsule:
Gelatin (20 kg) and concentrated glycerin (6 kg) were admixed in the presence of purified water (20 kg) at 70° C. to give homogeneous solution. (2R)-7-oxo-2-propyloctanoic acid (0.9 kg) was injected into soft capsule filling machine (rotary-type soft capsule filling machine (TYPE-H1 manufactured by KAMATA CO., LTD.)) to give wet soft capsules each containing (2S)-7-oxo-2-propyloctanoic acid. The obtained wet soft capsules were dried by tumble-dry and rack-dry sequentially, thereby obtaining above captioned soft capsules (2200 capsules) each containing 300 mg of (2S)-7-oxo-2-propyloctanoic acid.

Example 9

Injectable Solution (2):

(2R)-7-oxo-2-propyloctanoic acid (2 kg) and trisodium phosphate 12 hydrate (3.54 kg) were added into water for injection, and poured water for injection to 40 L. The obtained homogeneous solution was filtrated with sterilizing filter (Durapore 0.22 micrometer membrane), dispensed in 2 ml portions into plastic ampoules and then subjected to heat sterilization by autoclave (123° C., 15 minutes), thereby obtaining 20,000 ampoules each containing 100 mg of active ingredient.

INDUSTRIAL APPLICABILITY

The present invention is useful for drug medicine as described below.

The compound represented by formula (I) of the present invention is useful as therapeutic agent for a neurodegenerative disease, cause it has an improving property of astrocyte function, an improving property of brain function and/or an inhibiting property of S100β expression. Specifically, it is useful for treating and/or preventing a neurodegenerative disease such as Parkinson's disease, Parkinson's syndrome, Alzheimer's disease, Down's disease, amyotrophic lateral sclerosis, familial amyotrophic lateral sclerosis, progressive supranuclear palsy, huntington's disease, spinocerebellar degeneration, dentatorubral-pallidoluysian atrophy, olivopontocerebellar atrophy, corticobasal degeneration, familial dementia, frontotemporal dementia, senile dementia, diffuse Lewy body disease, striato-nigral degeneration, chorea-athetosis, dystonia, Meige's syndrome, late cortical cerebellar atrophy, familial spastic paraplegia, motor neuron disease, Machado-Joseph disease, Pick's disease, moyamoya disease, stroke (e.g., brain hemorrhage (e.g., hypertensive intracerebral hemorrhage), brain infarction (e.g., cerebral thrombosis, cerebral embolism), transient ischemic attack, subarachnoidal hemorrhage), neuronal dysfunction by cerebrovascular disorder (e.g., brain hemorrhage, brain infarction, transient ischemic attack, subarachnoidal hemorrhage), neuronal dysfunction by cerebrospinal injury, demyelinating disease (e.g., multiple sclerosis, Guillain-Barre syndrome, acute disseminated encephalomyelitis, acute parencephalitis, transverse myelitis), brain tumor (e.g., strocytoma), cerebrospinal disease associated with infection (e.g., cerebral meningitis, cerebral abscess, Creutzfeldt-Jakob disease, AIDS dementia), psychiatric disorder (e.g., schizophrenia, circulatory psychosis, nervous disease, psychosomatic disorder, epilepsy) and the like and neuropathy such as transient blindness (e.g., transient amaurosis), disturbance of consciousness, hemiplegia, sensory disturbance, homonymous hemianopsia, aphasia, alternate hemiplegia, two-side quadriplegia, vertigo, ear noises, nystagmus, double vision, coma and the like.

The invention claimed is:

1. A compound selected from the group consisting of (2R, 7R)-7-hydroxy-2-propyloctanoic acid, (2R,7S)-7-hydroxy-2-propyloctanoic acid and (2R)-8-hydroxy-2-propyloctanoic acid, a salt thereof, or a prodrug thereof.

2. The compound according to claim 1, which is obtained by chemical synthesis.

3. A pharmaceutical composition, which comprises: a compound represented by formula (I):

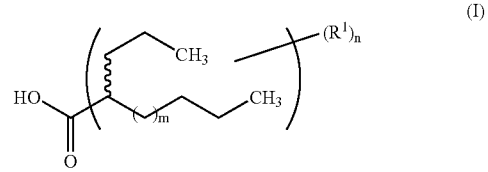

wherein
$R^1$ represents hydroxy or oxo,
⁓ indicates α-configuration, β-configuration or a mixture of these in an arbitrary proportion,
n represents an integer of 1 to 3, and
m represents an integer of 1 to 10; and
wherein two or more $R^1$'s are not bound to the same carbon atom other than the terminal carbon atom,
a salt thereof or a prodrug thereof,
in which said compound is a compound represented by formula (I-2):

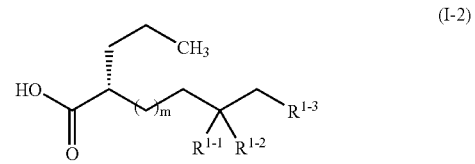

wherein
$R^{1-1}$ and $R^{1-2}$ are each independently a hydrogen atom or hydroxy, or
$R^{1-1}$ is taken together with $R^{1-2}$ to represent oxo,
$R^{1-3}$ represents a hydrogen atom or hydroxy,
m represents an integer of 1 to 10, and
⋯⋯ indicates α-configuration; and
wherein, when $R^{1-1}$ is taken together with $R^{1-2}$ to represent oxo, $R^{1-3}$ represents a hydrogen atom, and
a pharmaceutically acceptable additive agent.

4. A method for treating a neurodegenerative disease, which comprises administering to a mammal an effective amount of the compound represented by formula (I):

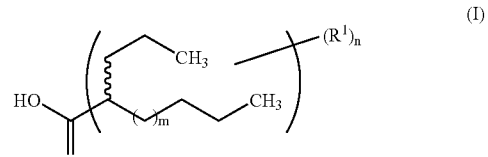

wherein
$R^1$ represents hydroxy or oxo,
⁓ indicates α-configuration, β-configuration or a mixture of these in an arbitrary proportion,
n represents an integer of 1 to 3, and
m represents an integer of 1 to 10; and
wherein two or more $R^1$'s are not bound to the same carbon atom other than the terminal carbon atom,
a salt thereof or a prodrug thereof, in which said compound is a compound represented by formula (I-2):

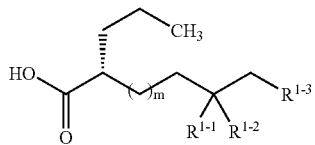

(I-2)

wherein
$R^{1-1}$ and $R^{1-2}$ are each independently a hydrogen atom or hydroxy, or
$R^{1-1}$ is taken together with $R^{1-2}$ to represent oxo,
$R^{1-3}$ represents a hydrogen atom or hydroxy,
m represents an integer of 1 to 10, and
⁝⁝⁝⁝ indicates α-configuration; and
wherein, when $R^{1-1}$ is taken together with $R^{1-2}$ to represent oxo, $R^{1-3}$ represents a hydrogen atom.

* * * * *